US005759768A

United States Patent [19]

Haseltine et al.

[11] Patent Number: 5,759,768
[45] Date of Patent: Jun. 2, 1998

[54] ASSAYS FOR FACTORS AFFECTING CIRCULARIZATION OF DNA, ASSAYS FOR FACTORS AFFECTING DNA INTEGRATION, FACTORS, AND USES THEREOF

[75] Inventors: William A. Haseltine; Christopher M. Farnet, both of Cambridge, Mass.

[73] Assignee: Dana Farber Cancer Institute, Boston, Mass.

[21] Appl. No.: 425,726

[22] Filed: Apr. 20, 1995

Related U.S. Application Data

[63] Continuation of Ser. No. 703,180, May 17, 1991, abandoned.

[51] Int. Cl.$^6$ .............................. C12Q 1/70; C12Q 1/68; C12N 5/10; C12N 7/00
[52] U.S. Cl. ............................ 435/5; 435/6; 435/235.1; 435/325
[58] Field of Search .............................. 435/5, 6, 240.2, 435/235.1, 325

[56] References Cited

U.S. PATENT DOCUMENTS

| 5,026,635 | 6/1991 | Ferguson et al. | 435/5 |
|---|---|---|---|
| 5,049,502 | 9/1991 | Humphries | 435/240.2 |

FOREIGN PATENT DOCUMENTS

WO92/03578  5/1992  WIPO .................. C12Q 1/70

OTHER PUBLICATIONS

Brown et al., Cell 49 1987 347–356.
Katz et al. J Virol 42 1982 346–351.
Pauza et al. J Virol 63 1989 3700–3707.
Pauza et al., *J. Virol.*, vol. 63, 1989, pp. 3700–3707.
Brown et al., *Cell*, vol. 49, 1987, pp. 347–356.
Katz et al., *J. Virology*, vol. 42, 1982, pp. 346–351.
R. Weiss, et al., "RNA Tumor Viruses," Cold Spring Harbor Laboratory, vol. 1, pp. 369–512 (1982).
Varmus, et al., Science, 216:812–820 (1982).
Fujiwara and Mizuuchi, Cell, 54:497–504 (1988).
Brown, et al., PNAS, 86:2525–2529 (1989).
Shank and Varmus, J. Virol., 25:104–114 (1978).
Barre-Sinoussi, et al., Science, 220:868–871 (1983).
Gallo, et al., Science, 224:500–503 (1984).
Levy, et al., Science, 225:840–842 (1984).
Popovic, et al., Science, 224:497–500 (1984).
Sarngadharan, et al., Science, 224:506–508 (1984).
Siegal, et al., N. England J. Med., 305:1439–1444 (1981).
Zagury, et al., Science, 231:850–853 (1986).
Ratner, et al., Nature, 313:277–284 (1985).
Sanchez-Pescador, et al., Science, 227:484–492 (1985).
Muesing, et al., Nature, 313:450–457 (1985).
Wain-Hobson, et al., Cell, 40:9–17 (1985).
Sodroski, et al., Science, 231:1549–1553 (1986).
Arya, et al., Science, 229:69–73 (1985).
Sodroski, et al., Nature, 321:412–417 (1986).
Sodroski, et al., Science, 227:171–173 (1985).
Feinberg, et al., Cell, 46:807–817 (1986).
Haseltine, et al., Journal of Acquired Immune Deficiency Syndrome, 1:217–240 (1988).
Cohen, et al., Nature, 334:532–534 (1988).
Wong-Staal, et al., AIDS Res. and Human Retro Viruses, 3:33–39 (1987).
Guyader, et al., Nature, 326:662–669 (1987).
Chakrabarti, et al., Nature, 328:543–547 (1987).
Lee and Coffin, J. Virol., 64:5958–5965 (1990).
Farnet and Haseltine, J. Virol., 65:1910–1915 (1991).
Farnet and Haseltine, PNAS, 87:4164–4168 (1990).
Kim, et al., J. Virol. 63:3708–3713 (1989).
Farnet, et al., Abstract of 6th International Conf. on AIDS, Abstract No. SA328.
Craigie, R., et al., Cell 62:829–837 (1990).
Farnet, C., et al., Journ. of Virol. 65:6943–6952 (1991).
Kreuzer, Kenneth N., Pharmac. Ther. 43:377–395 (1989).
Hirsch, M.S., The Journ. of Infectious Diseases 161:845–857 (1990).
Sherman, P.A., et al., Proc. Natl. Acad. Sci. USA 87:5119–5123 (1990).

*Primary Examiner*—Nancy Degen
*Attorney, Agent, or Firm*—David G. Conlin; Ronald I. Eisenstein; Dike, Bronstein, Roberts & Cushman, LLP

[57] ABSTRACT

An assay for factors that affect integration of DNA into target DNA is disclosed. Assays for methods of screening for factors which effect viral DNA circularization either by homologous recombination, end-to-end ligation, or autointegration, are also disclosed. A method for screening for factors which will enhance circularization rather than integration by testing cellular cytoplasmic fluid under conditions which permit circularization in the fluid is also described. Factors which effect integration and circularization are disclosed. Therapeutic methods for retarding viral infection are also described.

27 Claims, 25 Drawing Sheets

1-LTR Circle Formation

1-LTR circular intermediate full length linear

Amplifying Autointegration
Events by PCR 1) simple 2-LTR circles:

2) 1-LTR circles:

3) autointegration products:

joining of opposite DNA strands
at target site joining of same DNA strands
at target site

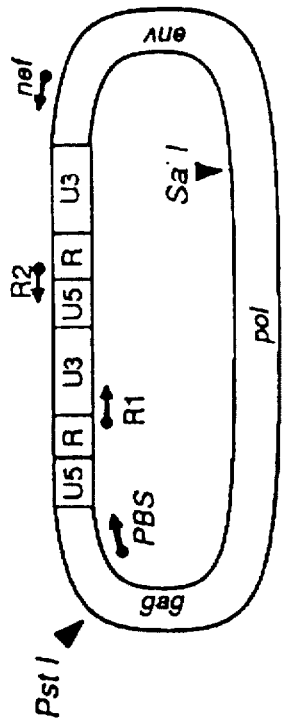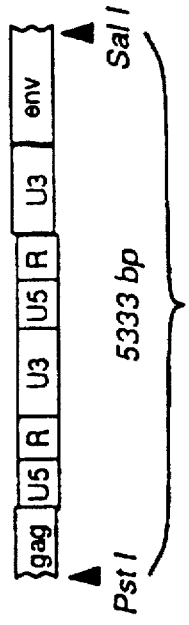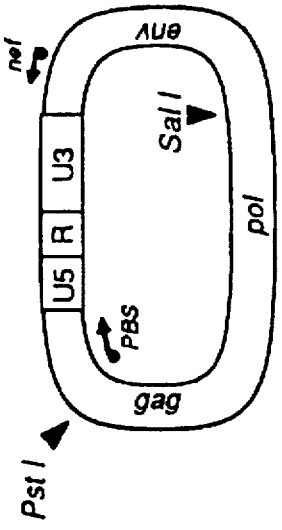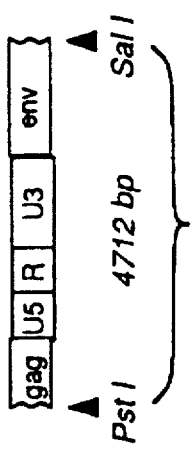
FIG. 9-2

5.

joining of opposite DNA strands

7.

xSal I, Pst I heterogeneous
LTR-containing
fragments

6.
joining of the same DNA strands

8.

xSal I, Pst I heterogeneous
LTR-containing
fragments

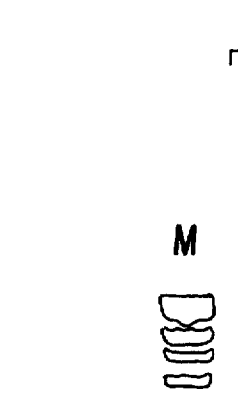
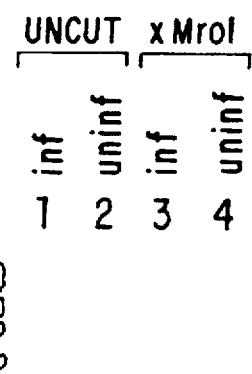
FIG. 24A
FIG. 24B
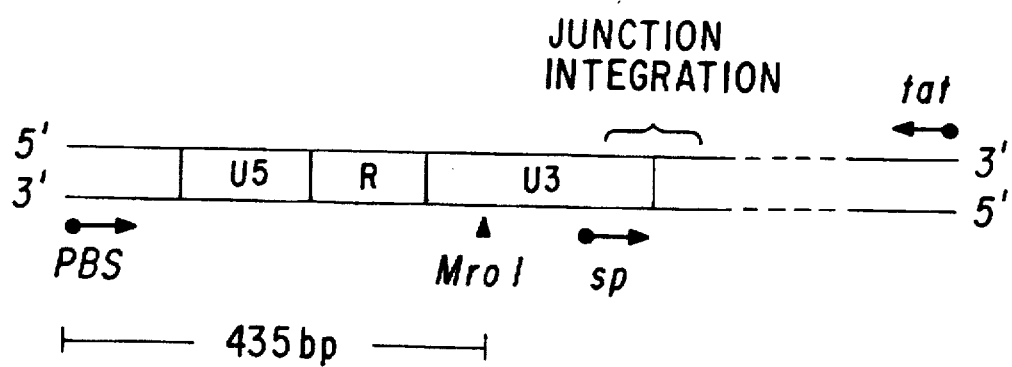
FIG. 24C

ASSAYS FOR FACTORS AFFECTING CIRCULARIZATION OF DNA, ASSAYS FOR FACTORS AFFECTING DNA INTEGRATION, FACTORS, AND USES THEREOF

This is a continuation of application Ser. No. 07/703,180 filed on May 17, 1991, now abandoned.

The present invention is directed to assays for compounds which promote or retard the circularization of DNA, either through autointegration, end-to-end ligation, or homologous recombination; assays for compounds which promote or retard DNA integration; the compounds and the uses of such compounds.

Cells infected with viruses, including DNA viruses and retroviruses, harbor a variety of DNA molecules derived from the infecting viral genome. With retroviruses, in the cytoplasm of the cell, reverse transcription of the viral RNA generates a linear, double-stranded DNA molecule containing the viral genes bounded by directly repeated sequences termed long terminal repeats (LTRs) [Varmus and Swanstrom, in R. Weiss et al., eds. *RNA Tumor Viruses*, Vol. 1, Cold Spring Harbor Laboratory, N.Y. (1982), pp. 369–512]. The nucleus of the infected cell contains several forms of viral DNA in addition to the linear DNA synthesized in the cytoplasm (FIG. 9). Viral DNA integrated into the host genome is identical in structure to the unintegrated linear molecule, expect for the absence of two base pairs from each LTR terminus at the sites of joining to host DNA [Varmus, *Science* 216:812–820 (1982)]. At least two forms of circular viral DNA are also found in the nucleus. The most abundant form contains a single copy of the LTR, while a smaller number of circles contain two LTRs. The integrated form and the circular forms are not found in the cytoplasmic portion.

Recent studies in a number of retroviral systems have provided convincing evidence that the linear unintegrated form of viral DNA is the direct precursor to the integrated provirus [Fujiwara and Mizuuchi, *Cell* 54:497–504 (1988); Brown et al., *Proc. Natl. Acad. Sci., USA* 86:2525–2529 (1989)]. The development of effective and efficient in vitro integration systems, and the analysis of in vitro reaction intermediates, would permit detailed information on the mechanism of provirus formation.

It would be desirable to have such an integration assay to screen for compounds which affect viral integration. A compound which hinders integration could be used therapeutically against viral infection.

Even less is known about the biochemical events involved in the circularization of viral DNA. While it has been demonstrated that the linear viral DNA synthesized in the cytoplasm is the precursor to the circular DNA forms found in the nucleus [Shank and Varmus, *J. Virol.* 25:104–114 (1978)], the mechanism of circularization remains unknown.

It is believed that one of the factors that increases the infectivity of these retroviruses, in particular, the human immunodeficiency virus (HIV), is the high efficiency with which it is integrated into cellular DNA. HIV-1 is the etiological agent of the acquired immune deficiency syndrome (AIDS) and related disorders. [Barre-Sinoussi, et al., *Science* 220:868–871 (1983); Gallo et al. *Science* 224:500–503 (1984); Levy et al., *Science* 225:840–842 (1984); Popovic et al., *Science* 224:497–500 (1984); Sarngadharan et al., *Science* 224:506–508 (1984); Siegal et al., *N. Engl. J. Med.* 305:1439–1444 (1981)]. This disease is characterized by a long asymptomatic period followed by the progressive degeneration of the immune system and the central nervous system. Studies of the virus indicate that replication is highly regulated, and both latent and lytic infection of the CD4 positive helper subset of T-lymphocytes occur in tissue culture, [Zagury et al., *Science* 231:850–853 (1986)]. The expression of the virus in infected patients also appears to be regulated as the titer of infectious virus remains low throughout the course of the disease. Molecular studies of the replication and genomic organization of HIV-I show that it encodes a number of genes [Ratner et al., *Nature* 313:277–284 (1985); Sanchez-Pescador et al., *Science* 227:484–492 (1985); Muesing et al., *Nature* 313:450–457 (1985); Wain-Hobson et al., *Cell* 40:9–17 (1985)]. Three of the genes, the gag, pol and env genes are common to all retroviruses. The genome also encodes additional genes that are not common to most retrovirus, the tat, rev (formerly referred to as art), nef, vif, vor and vpu genes [Sodroski et al., *Science* 231:1549–1553 (1986); Arya et al., *Science* 229:69–73 (1985); Sodroski et al., *Science* 227:171–173 (1985); Sodroski et al., *Nature* 321:412–417 (1986); Feinberg et al., *Cell* 46:807–817 (1986); Haseltine, W. A., *Journal of Acquired Immune Deficiency Syndrome* 1:217–240 (1988); Cohen, E. et al., *Nature* 334:532–534 (1988); Wong-Staal, F., et al., *AIDS Res. and Human Retro Viruses* 3:33–39 (1987) which are all incorporated herein by reference.]

Nucleotide sequences from viral genomes of other retroviruses, particularly HIV-2 and simian immunodeficiency viruses, SIV (previously referred to as STLV-III), also contain the structural genes including env as well as regulatory sequences such as tat, rev and nef [Guyader et al., *Nature* 326:662–669 (1987); Chakrabarti et al., *Nature* 328:543–547 (1987), which is incorporated herein by reference].

It would be desirable if there was a means to reduce the efficiency of this integration. Factors which accomplish this could be used therapeutically against the spread of retroviral infection. The circular form of the virus is not integrated into host DNA. Furthermore, the circular forms of viral DNA are not believed to be able to direct the formation of progeny virus. In particular, circles formed by autointegration have a disrupted viral genome, and are likely to represent dead-ends in the viral replication cycle. Accordingly, it would be desirable if there was an assay to screen for compounds which affect DNA circularization. It would also be desirable if there was a method to promote the circularization of such DNA rather than its integration.

We have now discovered such assays, compounds which retard DNA integration, and compounds which promote circle formation through autointegration, homologous recombination, and end-to-end ligation.

SUMMARY OF INVENTION

We have discovered a series of assays that can be used to screen for factors that effect DNA integration and circularization activities.

One method is for determining factors which affect cellular integration comprising testing cytoplasmic fluid by (a) incubating a DNA sequence which is capable of integration into a target DNA sequence in the fluid; (b) adding the target DNA sequence to the fluid, and (c) determining whether integration has occurred. In a preferred embodiment, the DNA sequence capable of integrating into a target DNA sequence preferably corresponds to an oncogenic sequence or a viral sequence. Preferably the sequence corresponds to a pathogenic viral sequence.

A method for determining factors which affect DNA circularization activities by testing cellular cytoplasmic fluid comprising the steps of: (a) contacting the fluid with a linear DNA sequence which is capable of homologous recombination, end-to-end ligation or autointegration, wherein the fluid does not contain a target DNA sequence; (b) adding a predetermined factor to the fluid; and (c) determining whether circularization has occurred is also described.

Another embodiment is for an assay to screen for factors which will enhance circularization activity rather than integration comprises testing cellular cytoplasmic fluid under conditions which permit circularization in the fluid by (a) contacting the fluid with a DNA sequence capable of circularization either by homologous recombination, end-to-end ligation, or autointegration ; (b) adding a target DNA sequence to the fluid; (c) adding a predetermined compound to the fluid and (d) determining the amount of integration and/or circularization that has occurred.

We have also discovered therapeutic methods for promoting circularization to retard DNA integration. Preferably this is used to retard the spread of viral infection. More preferably to retard the spread of retroviral infection. One such method involves increasing the level of free triphosphates in the cytoplasm. Preferably the triphosphate is adenosine triphosphate (ATP).

Factors which retard integration are also disclosed. These factors include inhibitors of topoisomerases.

BRIEF DESCRIPTION OF THE DRAWINGS

FIG. 10 is a time course of viral DNA synthesis in newly infected cells.

FIG. 12 shows sucrose gradiant sedimentation of viral DNA in cytoplasm extracts.

FIG. 13C is a graph showing a profile of linear viral DNA, viral p24 and total protein eluted from the column.

FIG. 24 shows PCR amplification of viral DNA purified from extracts incubated with ATP.

DETAILED DESCRIPTION OF THE INVENTION

Figure 1:
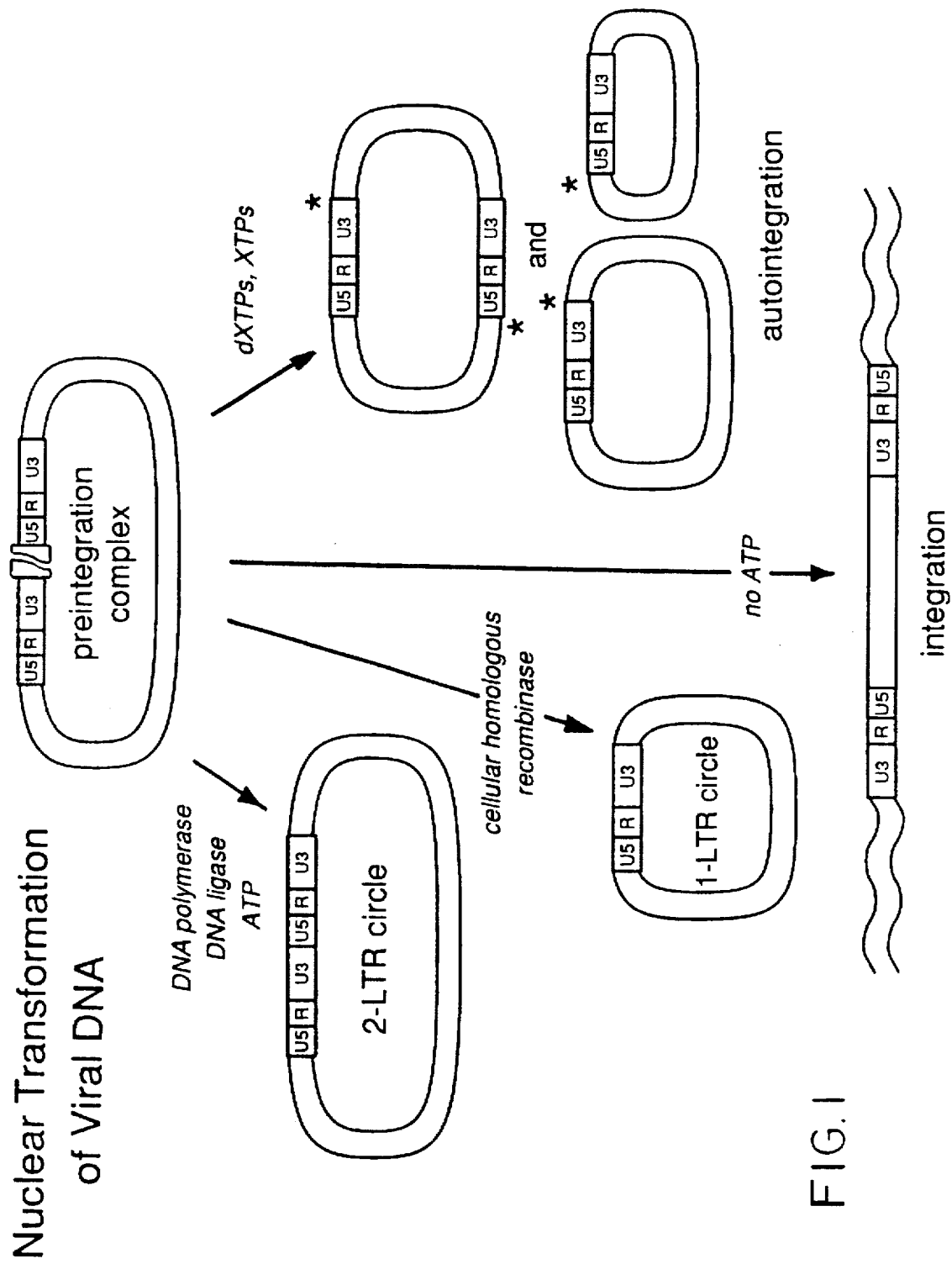
FIG. 1 is a schematic of nuclear transformation of viral DNA.
Figure 2:
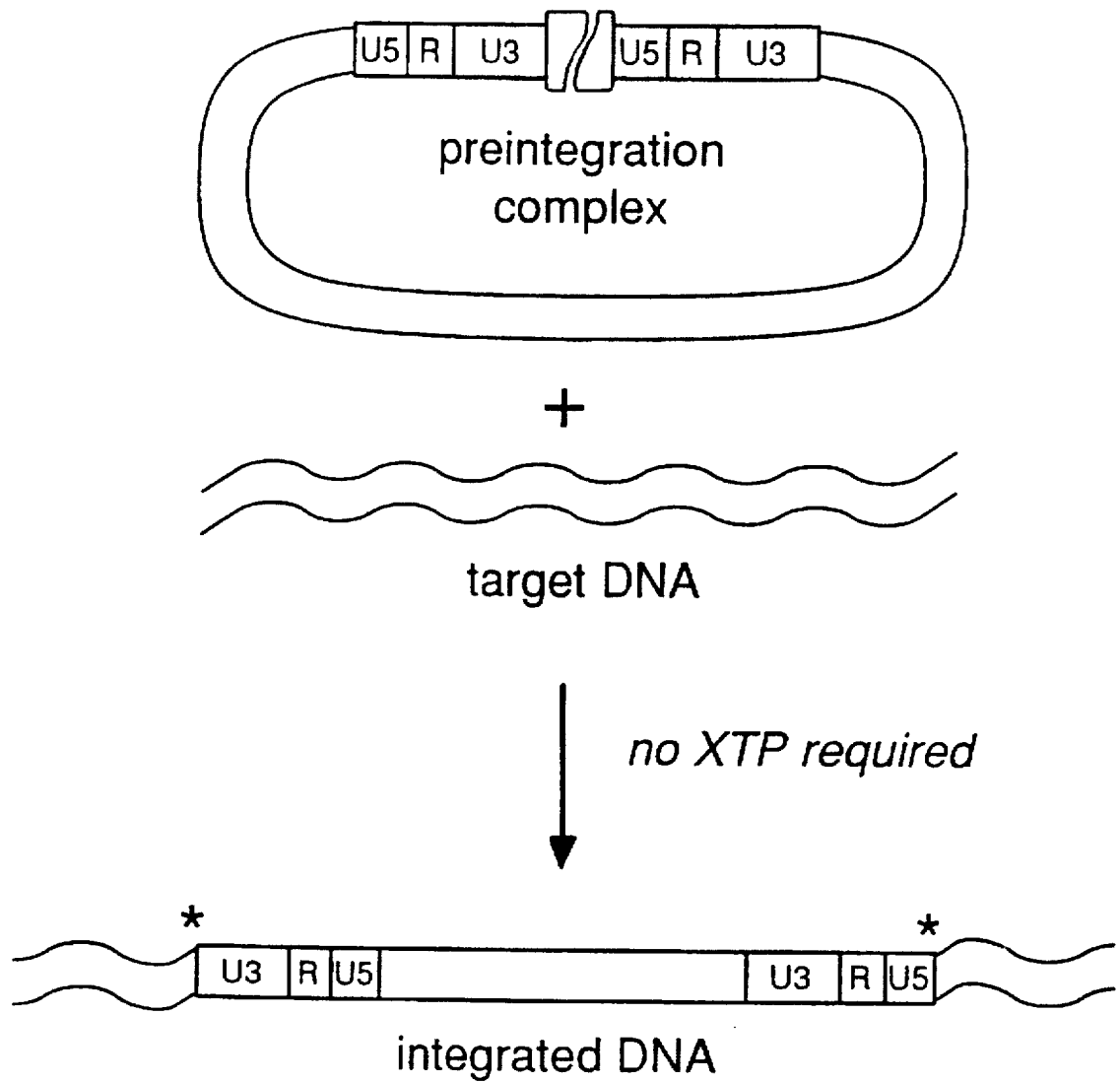
FIG. 2 is a schematic of integration of viral DNA.

We have discovered a series of assays that can be used to screen for compounds that affect DNA integration and/or circularization. We have also found compounds which influence such integration and/or circularization.

The present invention describes a method of determining factors which affect cellular integration which comprises testing cellular cytoplasmic fluid by (a) incubating the fluid with a DNA sequence which is capable of integrating into a target DNA sequence; (b) adding the target DNA sequence to the fluid; and (c) determining whether integration has occurred.

The above assay can be used to screen for compounds that affect integration of DNA into a target DNA. Although this assay can be used for screening for the integration of any DNA sequence which is capable of integrating into a target DNA sequence, it is preferably used to screen for a DNA sequence that corresponds to an oncogenic sequence or a viral sequence, either of a DNA virus or an RNA virus. As used herein an oncogenic sequence is a sequence whose presence in a cell can result in the malignant transformation of the cell. Such sequences are known in the art and include both oncogenes and altered suppressor genes. Preferably the assay is used to screen for viral integration. Still more preferably, the DNA sequence corresponds to a pathogenic virus DNA. More preferably still, the DNA sequence corresponds to a pathogenic retrovirus. Even more preferably, the DNA sequence corresponds to a lentivirus. Still more preferably the lentivirus is HIV-1, HIV-2 or SIV. Most preferably it is HIV-1 or HIV-2.

As used herein such DNA sequences can have conservative changes including deletions and additions, as well as some deletions or additions at either end from the native DNA sequence.

The target DNA sequence can be any DNA into which the other DNA sequence can integrate. Preferably the target DNA is mammalian DNA. More preferably, it is human DNA.

The assay can involve adding the DNA sequence to the cellular cytoplasmic fluid, for example cytoplasmic extract, and then adding the target DNA to the fluid, thereafter measuring the level of integration or adding the DNA sequence capable of integrating into the target DNA into cytoplasmic fluid already containing the target DNA sequences. This assay can also be used to select for factors (compounds) which accelerate or otherwise enhance integration as well as factors which retard integration. Compounds can be added to the cytoplasmic fluid to determine their effect on integration. This type of screen would preferably involve first establishing a baseline level of integration. Thus, compounds that provide some intermediate level of integration, can also be detected. Factors which increase integration efficiency can be useful in improving the efficiency of inserting a desired DNA sequence into a target DNA. Whereas, factors which retard integration can be used therapeutically to prevent integration of undesired DNA such as a pathogenic virus.

One preferred embodiment tests for factors affecting integration of viral DNA. One would preferably add viruses to uninfected cells susceptible to infection by that particular virus. Such cell lines can readily be determined by a person of ordinary skill in the art based upon the present disclosure and vary depending upon which viral DNA the DNA sequence corresponds to. For example, if one is testing for integration of HIV, one would choose an HIV susceptible cell line. For example, one that has CD4 receptors. These include T cells such as SupT1, Molt4, Jurkat, etc. One preferably uses cells that are highly susceptible to viral infection. For example, with HIV one preferably uses cells that have a large number of CD4 receptors such as SupT1 cells. At a predetermined time, the cytoplasmic extract is separated from the nucleus. This can be accomplished by any of a number of well known means. For example, the cells can be lysed and centrifuged for a predetermined time with the cytoplasmic extract separated from the nuclear extract. Preferably separation occurs before the cells have become chronically infected. Still more preferably, it is done within the first three cycles of viral replication after infection. Preferably one prepares extracts following a synchronouss infection. Thus, the cell is lysed preferably at a peak of viral replication for that cycle. Most preferably one would use a peak following the first or second viral replication cycles. Most preferably, one would use cytoplasm at the time of the first peak of viral replication, wherein replication is most synchronous.

Target DNA is then added to the cytoplasmic fluid, the reaction mixtures are incubated for a predetermined time at a predetermined temperature, for example, 37° C., and integration is determined by standard means. For example, Southern blot analysis, PCR, etc.

Baseline level of viral integration into the target DNA can readily be determined. For example, the viral DNA can be deproteinated by incubation with an enzyme such as proteinase K, the viral DNA extracted and analyzed by Southern blot analysis. The degree of integration can be determined by the shift of the linear DNA on Southern blots from its known characteristic position to a position corresponding to that DNA plus target DNA.

Factors that affect the efficiency of the in vitro integration reaction can readily be screened. As aforesaid, one can add a pre-selected compound to the fluid before the target DNA is added or afterwards to determine its effect on integration. By comparing the results with a baseline level, qualitative analysis of such factors can readily be made. Factors which affect integration can also be studied by rendering the factor(s) in the cytoplasmic fluid which promote integration inert and then adding factors to the fluid to determine their effect on integration. For example, one can fractionate the extract and then add desired factors to the purified extract.

This assay results in being able to achieve integration levels in the cytoplasmic extract that are preferably about 80%, more preferably about 85%, even more preferably about 90%, still more preferably about 95%, and even more preferably about 98%. Being able to achieve such a high level of integration permits a screening for a wide range of compounds that adversely affect integration.

Using this assay we have found that inhibitors of DNA topoisomerases had a negative effect on integration. Such inhibitors of DNA topoisomerases include inhibitors of topoisomerase I, for example the alkaloid camptothecin. These inhibitors also include inhibitors of topoisomerase II such as cumarins which include novobiocin, coumermycin, $A_1$, and chlorobiocin; quinolones such as nalidixic acid, oxolinic acid, norfloxacin; acridines such as m-AMSA; anthracyclines such as 5-iminodaunorubicin; ellipticines such as 2-Me-9OOH-E$^+$; epipodophyllo toxins such as VP-16 and VM-26. One would add these compounds in a dose sufficient to retard integration.

We observed very little circle formation in these integration assays. Accordingly, with the high level of integration efficiency found in the cytoplasmic extract, we believed it highly unlikely that this assay could also be used to assay for the competing reactions that lead to viral DNA circularization. We thought it particularly unlikely that one would be able to look for autointegration reactions, since as aforesaid integration with target DNA had an efficiency greater than 98%.

Surprisingly, we found that one could use the same assay only without target DNA sequence in the cytoplasmic extract to study the circularization activities. We found that one could determine factors which affect circularization by testing cellular cytoplasmic fluid by (a) contacting the fluid with a DNA sequence which is capable of circularization either by homologous recombination, end-to-end ligation or autointegration, wherein the fluid does not contain a target DNA sequence; (b) adding a predetermined factor to the fluid; and (c) determining whether circularization has occurred.

Previously it had been thought that using cytoplasmic assays, one could not detect the ciruclarization reactions because some cellular factor from the nucleus was needed for such activity. Indeed, since very little autointegration is seen in vivo it would be expected that some factor in the cell extract would limit the degree of autointegration. However, the high level of autointegration our assay found, surprisingly establishes otherwise.

The DNA sequence capable of circularization preferably corresponds to an oncogenic sequence or a viral sequence of a DNA virus or an RNA virus. Preferably, this sequence corresponds to a viral sequence. More preferably, it corresponds to a pathogenic viral sequence. Still more preferably the virus is a retovirus, e.g. HTLV, HIV, etc. Even more preferably the retrovirus is a lentivirus. Preferably the lentivirus is HIV-1, HIV-2 or SIV. More preferably the lentivirus is HIV-1 or HIV-2.

The presence of target DNA in the cytoplasmic fluid competes with the circularization activities. Accordingly, it is possible to screen for factors which will enhance circularization rather than integration by testing cellular cytoplasmic fluid under conditions which permit circularization in the fluid by (a) incubating in the fluid a DNA sequence which is capable of circularization, either by homologous recombination, end-to-end ligation, or autointegration;
(b) adding a target DNA sequence to the fluid;
(c) adding a predetermined compound to the fluid; and
(d) determining the amount of integration and/or circularization that has occurred. The order of steps (a)–(c) can be varied.

Determination of quantitative and qualitative levels of integration and/or circularization activity can readily be performed by the skilled artisen based upon the present disclosure. For example, using Southern blot analysis, or PCR and comparing the results obtained with expected results for integration or circularization.

Using the circularization assay with, e.g., a DNA sequence corresponding to a virus, for example, HIV, and looking at the activity of circularization, all of the major types of circular viral DNA normally present in the nucleus of infected cells can be formed in cytoplasmic extracts, such as in cells newly infected with HIV-1. In the above example, the circular reaction products included 1-LTR circles, 2-LTR circles formed by joining of the ends of the linear DNA, and 2-LTR circles formed by autointegration. Such DNA sequence can be added to the cytoplasmic fluid by any of a wide variety of means. Preferably, with a DNA sequence corresponding to a viral sequence, for example a retrovirus such as HIV, one would use viral sequences to infect the cell. Preferably, one would use the same method as described above with reference to the integration assay.

Figure 3:
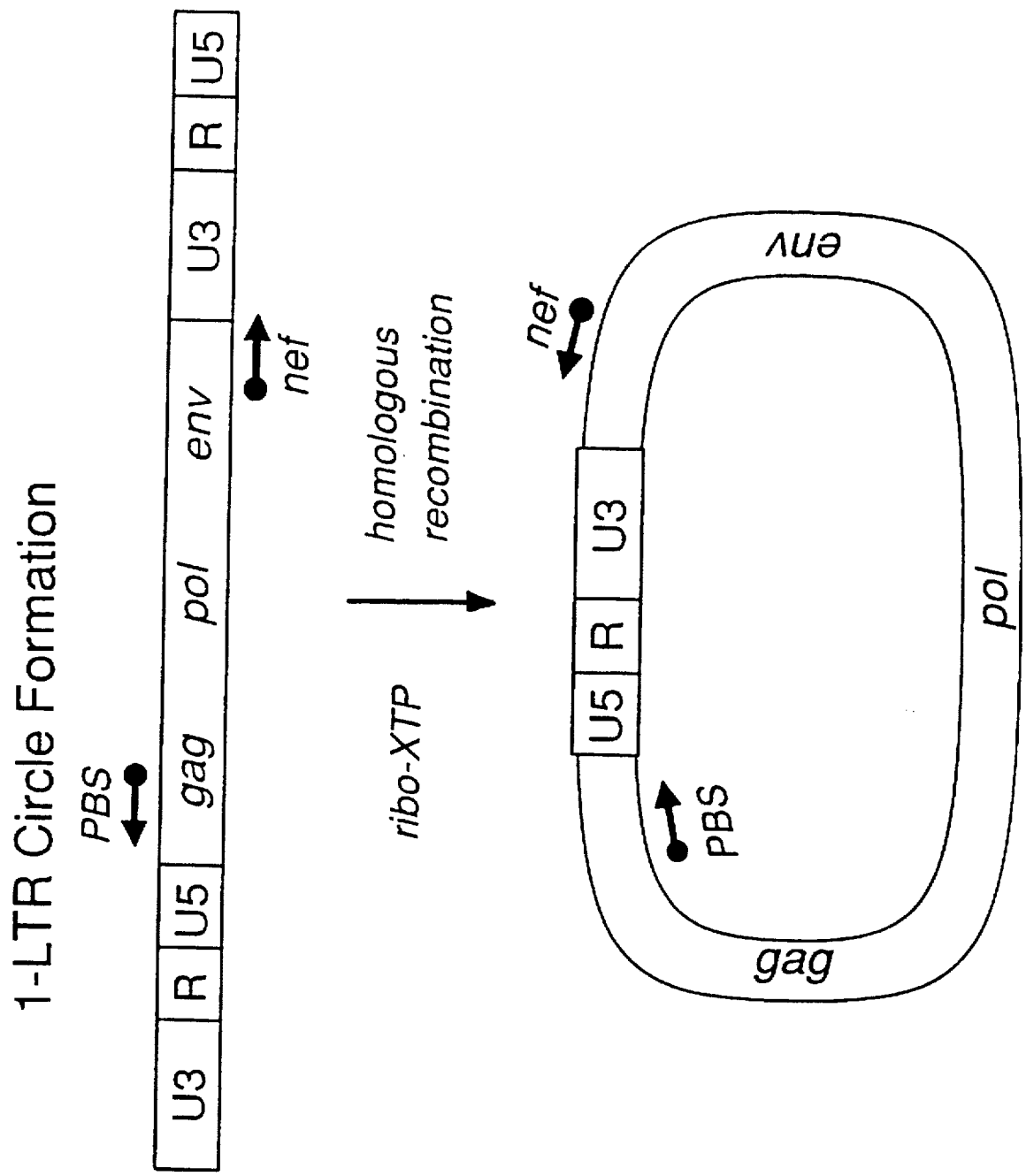
FIG. 3 a is schematic of 1-LTR circle formation.
Figure 4:
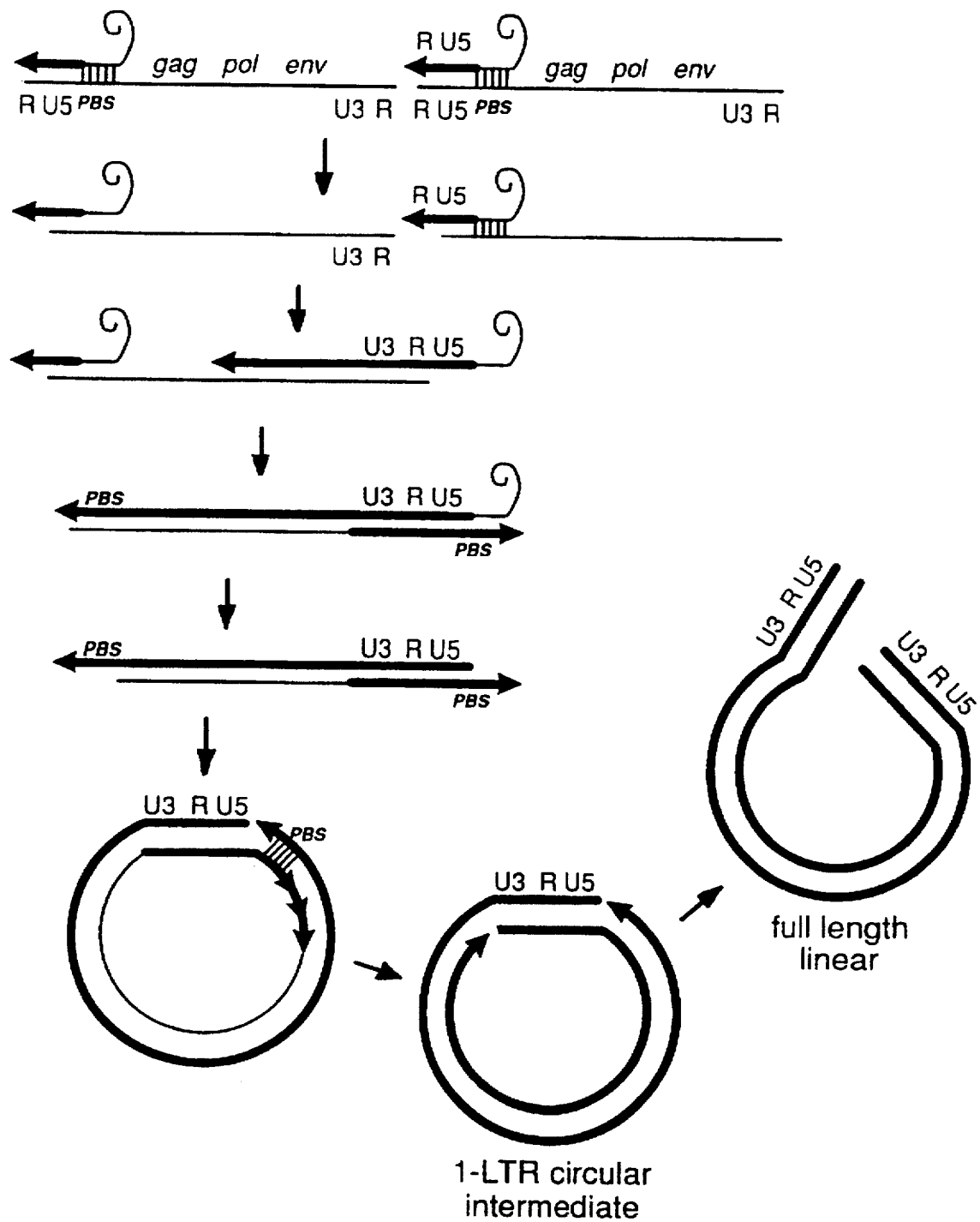
FIG. 4 is a schematic of one proposed method of 1-LTR circle formation.
Figure 5:
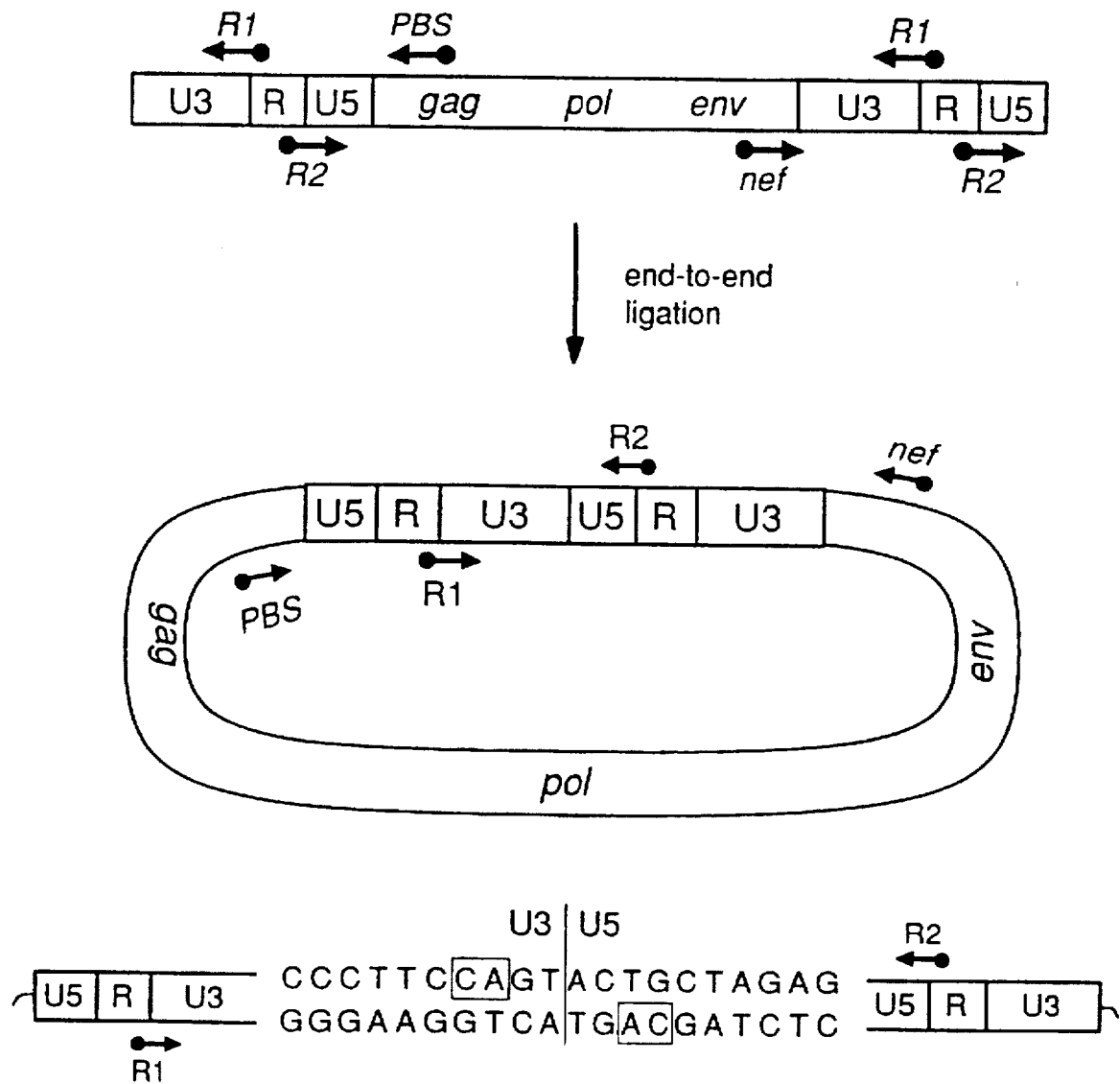
FIG. 5 is a schematic of simple 2-LTR circle formation.
Figure 6:
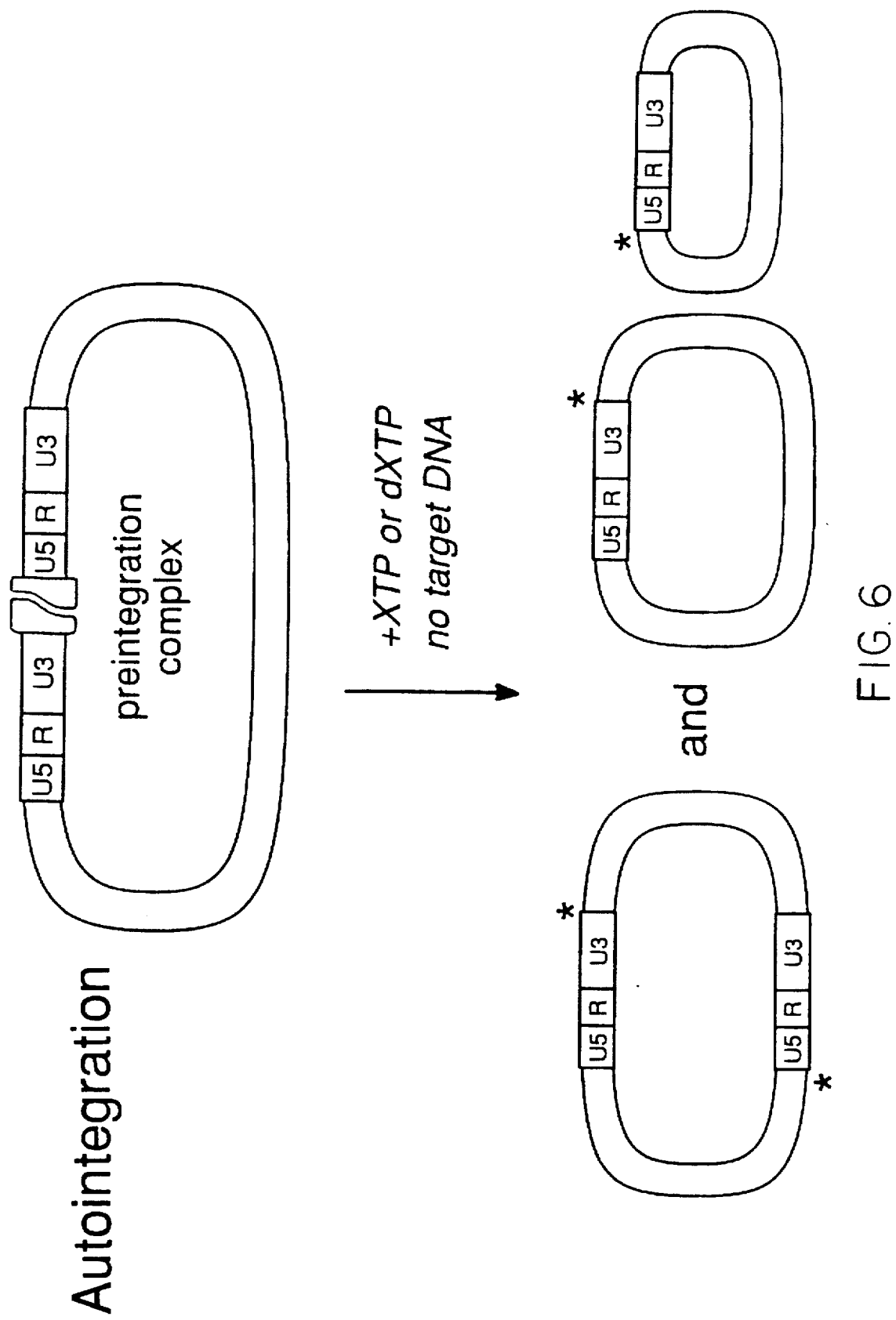
FIG. 6 is a schematic of circle formation by autointegration.

Circle formation is shown in FIG. 1. Circles containing one LTR (1-LTR) have been proposed to arise either from homologous recombination between the LTRs present on the linear viral DNA molecule (FIG. 3), or from a circular intermediate in the formation of the linear molecule during reverse transcription (FIG. 4). Circles with two tandem LTRs (2-LTR), on the other hand, are presumed to arise by the direct ligation of the ends of the linear DNA molecule (FIG. 5). Yet another class of circular DNA molecules containing two LTRs appears to arise from intramolecular integration (autointegration) events, presumably mediated by the viral integrase (FIGS. 6 and 9) [Lee and Coffin, J. Virol., 64:5958–5965 (1990)].

Time course analysis of the appearance of viral DNA forms in the nucleus following a single round of infection indicates that the linear viral DNA molecules undergo rapid transformation soon after entry into the nucleus [Kim, et al., J. Virol., 63:3708–3713 (1989)and Farnet and Haseltine, Proc. Natl. Acad. Sci. USA, 87:4164–4168 (1990)]. The concentration of linear DNA in the nucleus remains relatively constant and low, while the unintegrated circular forms and integrated proviruses accumulate with time. These observations suggest that once the linear viral DNA enters the nucleus, it either stably integrates into the host DNA or forms circular molecules which no longer have the capacity to integrate.

Figures 1, 9:
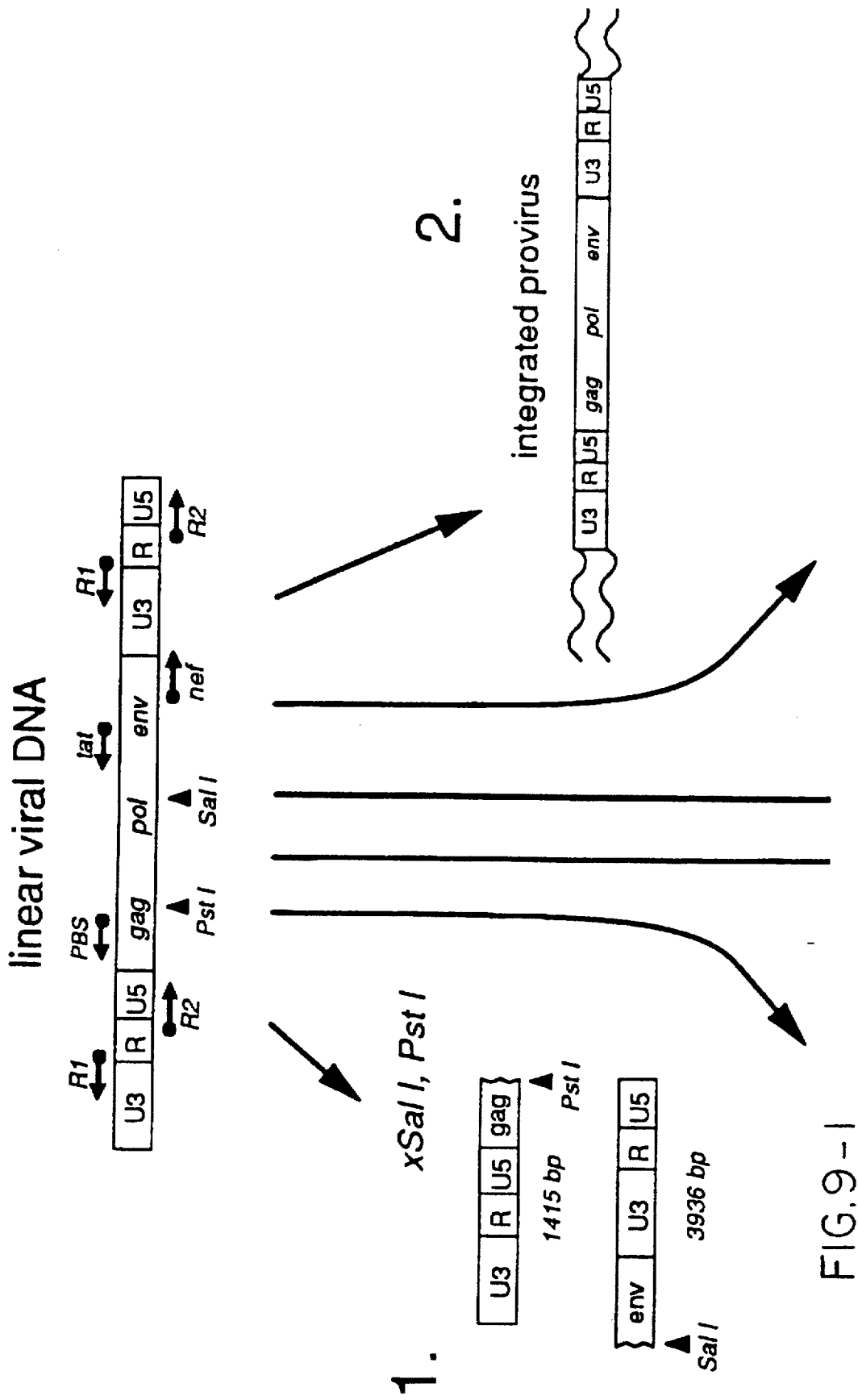
FIG. 9 is a schematic representation of events leading to circle formation and include 1-LTR circles, simple 2-LTR circles, and autointegration circles.
Figure 9:
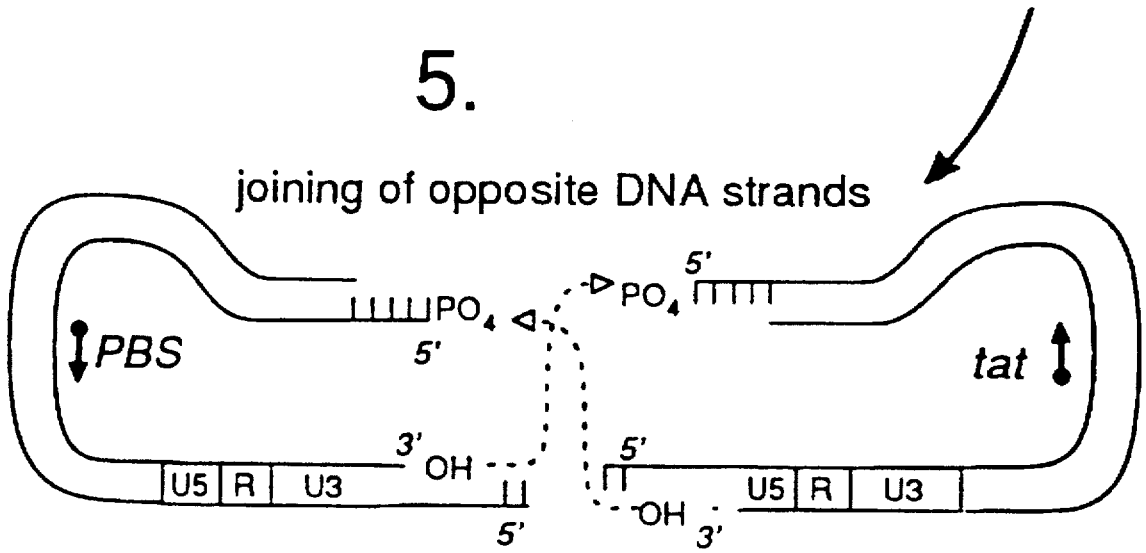
Figure 3:
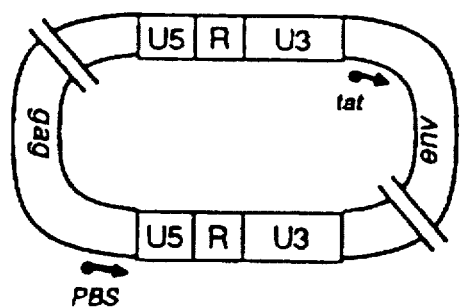
Figure 9:
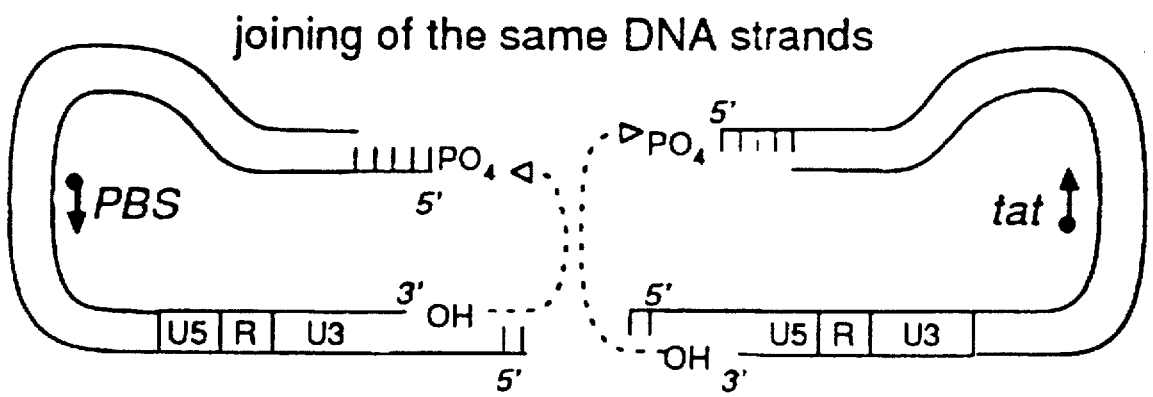
Figure 4:
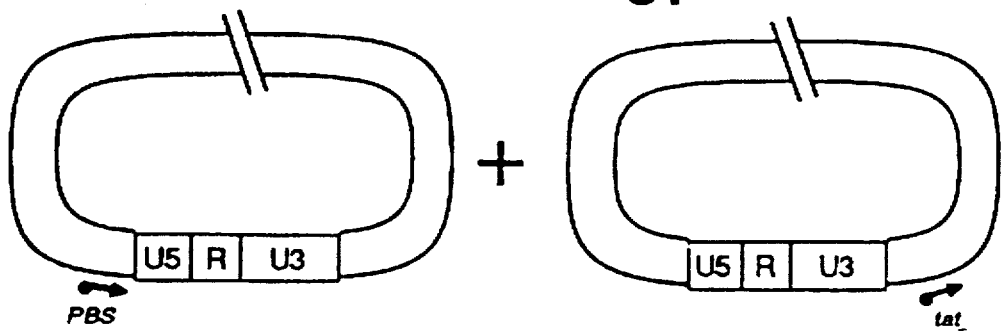

The different forms of circular viral DNA can be distinguished by analysis of the LTR-containing fragments generated by restriction endonuclease digestion (diagrammed in FIG. 9). Digestion of the circular viral DNA with enzymes that cut at sites bordering the LTRs is predicted to yield two DNA fragments, not found in digests of linear viral DNA, that differ in size by the length of the LTR. The smaller fragment, containing a single copy of the LTR, is derived from the 1-LTR circular viral DNA. The larger fragment contains two tandem copies of the LTR, and is derived from 2-LTR circles formed by end-to-end joining of the linear viral DNA (referred to as simple 2-LTR circles). Two types of circular DNA products are predicted to result from the autointegration of viral DNA depending upon the orientation of the DNA strand-joining reaction (lower part of FIG. 9). Joining of the 3'-hydroxyl terminus of each LTR to the 5'-phosphate of the opposite strand of viral DNA at the site of target cleavage will result in the formation of a circular molecule containing an inversion of viral sequences between two non-tandem LTR's (right side of FIG. 9). These products will be linearized by the restriction enzymes that cut viral DNA once, yielding molecules having the same size as the full length linear form of viral DNA. Digestion of these circular products with enzymes that cut viral DNA more than once is expected to yield LTR-containing DNA fragments of heterogeneous lengths, as the site of integration within the viral DNA is not constant. Alternatively, the autointegration reaction may result in the joining of the 3'-hydroxy terminus of each LTR to the 5'-phosphate of the same strand of viral DNA at the site of target cleavage (left side of FIG. 9). This type of event will generate a pair of circles of various sizes, each of which will be smaller than genome length and contain a single LTR. Digestion of these autointegration products with restriction enzymes that cut viral DNA either singly or multiply is predicted to yield a heterogenous mixture of LTR-containing DNA fragments.

All of the major reaction products of viral DNA normally found in infected cells can be generated in cell extracts in vitro using the present assay. Using these assays we were able to determine that certain cellular factors were required for the formation of 1-LTR and simple 2-LTR circles, while the viral integrase appeared to be sufficient for the formation of 2-LTR circles by autointegration.

Since circle formation, particularly circularization by autointegration, retards integration, one therapeutic method of inhibiting or alleviating viral infectivity is by promoting circle formation. We similarly believe that by promoting circularization in transformed cells it is possible to prevent oncogenic sequences from integrating into neighboring cells DNA. One method of accomplishing this is by increasing the free level of triphosphates in the cytoplasm. Preferably the triphosphate is a nucleoside triphosphate such as adenosine triphosphate (ATP), derivatives thereof such as deoxyadenosine triphosphate (dATP) and the nonhydrolyzable analogue ATPγs, dideoxyadenesine triphosphate (ddATP), etc, guanosine triphosphate (GTP), cytosine triphosphate (CTP), etc. More preferably the triphosphate is ATP or a derivate thereof.

The typical level of ATP in cells is about 1 mM, but this is most likely compartmentalized, thus in certain places in the cell the level will be much lower or much higher. Our results indicate that autointegration circle formation is sensitive at either extreme. Thus, it is not surprising that such circles are not typically found in large quantities in vivo.

One method of regulating the free ATP level is by the use of vessels such as liposome to deliver ATP to the cell. For example, in dealing with a retrovirus such as HIV one could construct a liposome with the envelope glycoprotein on it to have it preferentially seeks cells susceptible to viral infection. One would add ATP in an amount sufficient to reach a level of about 1 mM in the cytoplasm.

Another method of regulating free ATP levels is by adding compounds that increase or decrease ATP levels as needed. For example to increase ATP levels one can add RNA synthesis inhibitors such as actinomycin D, 3'-deoxyadenosine (cordecypin); inhibitors of purine synthesis such as methotrexate which can increase ATP pools; and ribonucleotide reductase inhibitors such as hydroxyurea. One can also add nucleosides. For example, using thymidine builds up thymidine triphosphate levels, while using uridine increases UTP levels. Ribavirin would also be useful. These compounds are added in an amount sufficient to change triphosphate levels in the cytoplasm.

We have found the following conditions affecting circularization in vitro:

|  | ATP | other XTPs | dXTPs | [KCl] optimum | [ATP] optimum |
| --- | --- | --- | --- | --- | --- |
| 1-LTR | + | +/− | +/− | 125 mM | 2 mM |
| Simple 2-LTR | + | − | − | N.D | N.D |
| Autointegration | + | + | + | 150–175 mM | 1 mM |

To promote 1-LTR circularization one would preferably add a triphosphate, more preferably ATP or a derivative thereof, most preferably ATP, at a concentration of about 1.0 mM to about 5 mM, more preferably about 1.5 mM to about 3.0 mM and still more preferably at about 1.75 to about 2.5, and most preferably about 2 mM. Preferably the KCl level is about 50 mM to 200 mM, more preferably about 100 to 150 mM, and most preferably about 125 mM.

To promote autointegration circularization, one would add a triphosphate, preferably ATP or a derivative thereof, more preferably ATP or ATPγS, still more preferably ATP, at a concentration of about 0.5 mM to about 2 mM, more preferably about 0.5 mM to about 1.5mM, still more preferably about 0.75 mM to about 1.25 mM and most preferably about 1 mM. The KCl level is preferably from about 75 to about 250 mM KCl, more preferably from about 100 to about 225 mM KCl, still more preferably from about 125 to 200 mM KCl and most preferably about 150–175 mM KCl.

Similarly, increasing the levels of viral integrase in the cytoplasm should enhance autointegration circles. Other factors that can be used in larger levels to promote circularization include reverse transcriptase, preferably viral reverse transcriptase, and DNA ligase. Preferably, such compounds would be combined with increasing the level of triphosphates, more preferably ATP, still more preferably ATPγS.

One could also add a compound that preferentially retards integration to target DNA to a greater extent than stopping autointegration.

Formation of all types of circular viral DNA molecules in vitro appears to require addition of nucleoside triphosphates to the cytoplasmic extracts. Adenine nucleoside triphosphates were the most effective inducers of circularization; however, all of the ribo-, deoxyribo-, and dideoxyribonucleoside triphosphates tested induced the circularization of viral DNA to some extent. The triphosphate moiety of these compounds was the most important determinant of the ability to induce circularization, as none of the nucleoside diphosphates or monophosphates tested induced the formation of circular DNA. All of the nucleoside triphosphates tested were able to induce the formation of 2-LTR circles by autointegration, but only some induced the formation of 1-LTR and simple 2-LTR circles.

The effect of nucleoside triphosphates on the formation of circular viral DNA was not previously disclosed. Although the formation of circular viral DNA in extracts of cells infected with avian leukosis virus has been described [Lee and Coffin, *J. Virol.*, 64:5958–5965 (1990)], some experiments were performed with ATP and phosphocreatine/creatine phosphokinase added to the cell extracts, which induced the formation of circular viral DNA, but not in others, such as the autointegration and viral DNA circularization experiments.

The integration and circularization assays can be used to assay for the ability of cellular factors to enhance circle formation. This assay can be used to find other factors which can be used therapeutically. For example, preintegration complexes purified by gel filtration chromoatography supported the formation of 1-LTR and simple 2-LTR circles only after the addition of cytoplasmic extracts from uninfected cells, which contained the cellular factors necessary. Furthermore, these two types of circular DNA were formed when deproteinated linear viral DNA was added to cytoplasmic extracts of uninfected cells. These results provide direct evidence that circular retroviral DNA can be formed by host proteins. Thus by this assay the particular cellular factor(s) can readily be found. One would inactivate the cellular factor(s) in the cytoplasmic fluid which promote homologous recombination such as circularization, using standard techniques, e.g., deproteinization, fractionation, etc. Thereafter, one would add factors from the cell back, for example, proteins from cytoplasm, to the fluid to determine their effect. For example, one can fractionate cytoplasmic extracts and assay fractions for the ability to promote the circularization of viral DNA.

As aforesaid, viral integrase protein was responsible for mediating the autointegration of viral DNA in vitro. This is shown by PCR amplification and DNA sequence analysis of autointegration reaction products which demonstrated that the ends of the linear viral DNA molecule were joined to target sequences at the highly conserved CA dinucleotide characteristically joined to target DNA during viral integration in vivo and in vitro. Second, preintegration complexes purified by gel filtration chromatoregraphy, which contain integrase as the sole viral protein component [Farnet and Haseltine, *J. Virol.*, 65:1910–1915 (1991)], were able to mediate the autointegration of viral DNA at efficiencies comparable to complexes present in unfractionated extracts. Third, deproteinated viral DNA was not a substrate for autointegration when added to extracts of uninfected cells under conditions which allowed the formation of the other circular forms of DNA.

Autointegration and integration into heterologous DNA targets are competing pathways as shown by the fact that autointegration was effectively competed by the presence of a high concentration of target DNA during the circularization reaction. Consequently, by accelerating autointegration, one will deaccelerate integration into target DNA. The relative yields of the circular DNA products formed in vitro depended upon the reaction conditions and upon the presence or absence of heterologous target DNA. In the absence of added target DNA, approximately equal amounts of 2-LTR and 1-LTR circles were formed. Under these conditions, most of the 2-LTR circles were the result of autointegration events mediated by the viral integrase, while only a small amount of simple 2-LTR circles were detected. Autointegration events were specifically inhibited by adding target DNA to the circularization reactions. In the presence of added target DNA, most of the circular viral DNA formed was of the 1-LTR type. The small amount of 2-LTR circles generated under these conditions resulted entirely from end-to-end joining of the linear viral DNA. The latter pattern of circular viral DNA, consisting of a large amount of 1-LTR circles and a much smaller amount of simple 2-LTR circles, is characteristic of the relative amounts of circular viral DNA normally found in the nucleus of infected cells [Farnet and Haseltine, *Proc. Natl. Acad. Sci. USA*, 87:4164–4168 (1990)]. One LTR circles are the first circular form of viral DNA to appear in the nucleus following a single round of infection with HIV-1, and quickly become the most abundant form [Kim, et al., *J. Virol.* 63:3708–3713; Farnet and Haseltine, *Proc. Natl. Acad. Sci. USA*, 87:4164–4168 (1990)]. Autointegration events appear to be rare during the course of HIV-1 replication, as most or all of the 2-LTR circles formed in vitro are simple 2-LTR circles. However, autointegration events were amplified by PCR using unintegrated viral DNA from cells acutely infected with HIV-1 as substrate, indicating that autointegration does occur in vivo.

Autointegration events disrupt the structural integrity of the viral genome and are therefore likely to be lethal to the virus. Autointegration may be inhibited in vivo by the high concentration of target DNA present in the nucleus. No such inhibition of autointegration would be expected to occur during the time that the viral preintegration complex is present in the cytoplasm of the cell. Thus, it is preferable to target promoting autointegration in the cytoplasm rather than nucleus. The present assays as discussed are useful in identifying compounds capable of stimulating the autointegration of viral DNA before it has entered the nucleus of the cell. Furthermore, the experiments presented here show that the balance of integrated DNA to unintegrated circular DNA depends upon the relative rates of competing integration and circularization reactions. Since the replication of HIV-1 and most other retroviruses requires the integration of viral DNA into host DNA, compounds which alter the activity of the enzymes which govern these different processes and which favor circularization over integration may inhibit retroviral replication. The present assays teach how to screen for such compounds.

For most retroviruses, 1-LTR circle represent the most abundant form of circular viral DNA generated during the course of replication. The circularization of purified linear viral DNA in extracts form uninfected cells provides strong evidence that 1-LTR circles result from host-mediated homologous recombination between the LTRs on linear viral DNA, although alternative models exist. Full-length linear viral DNA, containing two complete LTRs, is capable of forming 1-LTR circles in vitro, either as a part of the preintegration complex, or as purified DNA added to uninfected cell extracts.

These results show that a homologous recombination activity is present in cytoplasmic extracts of cells. Circular viral DNA is typically not formed in the cytoplasm of infected cells in vivo, thereby indicating that the host recombination enzymes are confined to the nucleus. This would suggest that the activities responsible for the formation of 1-LTR circles are nuclear enzymes that leak into the cytoplasmic extracts during the cell fractionation procedures. Similarly, the host functions responsible for the formation of simple 2-LTR circles would appear to be nuclear in origin. Formation of simple 2-LTR circles appears to require two factors. A DNA polymerase function would be required to fill in the two nucleotide gap at each 3'-terminus of the viral DNA generated by the action of the viral integrase. The viral reverse transcriptase may serve the filling-in function in vivo. The resulting blunt-ended DNA molecules would then serve as efficient substrates for joining by a host DNA ligase. Our assay demonstrates that such circularization can occur in the cytoplasm and indicates that one can prevent viral integration by forming circles in the cytoplasm.

The present invention is further illustrated by the following examples. These examples are provided to aid in the understanding of the invention and are not to be construed as a limitation thereof.

GENERAL

Preparation of Cell Extracts.

The chronically HIV-1 infected Molt IIIB human T cell line (HTLV IIIB virus strain) was the source of virus for cell-free infections. This human T cell line constitutively produces a low level of the HTLV-111B strain of HIV-1. Culture supernatant containing a high concentration of virus was prepared by incubating $300 \times 10^6$ Molt IIIB cells in 50 ml fresh RPMI 1640 medium containing 20% fetal calf serum and 10 ng of phorbol 12-myristate 13-acetate per ml for 20–24 hours. Cells were removed by centrifugation, and the supernatant, containing approximately 14–18 µg of p24 viral core protein per ml, was used to resuspend $100 \times 10^6$ cells of the human SupT1 T cell line. Cytoplasmic extracts (3 ml) were prepared 4–4.5 hours post-infection, by a modification of the procedure of Brown et al., *Cell* 49: 342–356 (1987).

At specified times after infection, cells were washed twice with buffer K (20 mM Hepes, pH 7.4, 150 mM KCl, 5 mM $MgCl_2$, 1 mM dithiothreitol, 25 mM aprotinin) and then lysed at a concentration of $33 \times 10^6$ cells per ml in the same buffer containing 0.025% digitonin or 0.025% Triton X-100. Cells were extracted for 10 minutes at room temperature, and the lysate was centrifuged at $1000 \times g$ for 3 minutes, and is referred to as "cytoplasmic extract". Cytoplasmic extract was the source of viral DNA for analyses in the assays described below. The pellet from the initial low-speed centrifugation contained cell debris and intact nuclei and is called the "nuclear pellet". Cell extracts from uninfected SupT1 cells were prepared in the same manner.

Fractionation of Cell Extracts.

Viral preintegration complexes were partially purified from cytoplasmic extracts by Sephacryl S400 gel filtration chromatography. Cytoplasmic extracts (0.8 ml) were loaded onto a 22-ml Sephacryl S400 (Pharmacia) column, 28 cm in height, equilibrated in buffer K containing 0.5% Triton X-100 at 4° C. Fractions (0.5 ml) were collected at a flow rate of approximately 0.2 ml/min.

Sucrose Gradient Sedimentation

S400 column fractions containing viral DNA were pooled, and 1.5 ml was layered on 12-ml gradients of 15 to 30% sucrose in buffer K-0.5% Triton X-100 and centrifuged at 35,000 rpm for 3 hours at 4° C. in a Beckman SW41 rotor. Fractions (1 ml) were collected from the bottom of the gradient.

Analysis of Viral DNA.

DNA Preparation.

Viral DNA present in cytoplasmic extracts was deproteinated by incubation with proteinase K (1 mg/ml)/10 mM EDTA/0.5% SDS for 1 hour at 55° C. Samples were extracted successively with phenol/chloroform [1:1 (vol/vol)] and chloroform. DNA was ethanol-precipitated, washed with 70% ethanol, resuspended in 10 mM Tris.HCl (pH 7.4), and treated with RNase A (20 µpg/ml)for 1 hour at 370° C. before analysis by agarose gel electrophoresis and Southern blotting.

For analysis of unintegrated viral DNA in the nucleus of infected cells, low molecular weight DNA was isolated from nuclear pellets of cell extracts by the method of Hirt [J.Mol.Biol., 26: 5707–5717 (1967)]. Samples were treated with RNase A (20 µg/ml) for 30 minutes at 37° C., extracted with phenol/chloroform and then with chloroform, and precipitated with ethanol.

Southern Blot Analysis.

DNA samples were layered on 0.8% agarose gels and electrophoresed at 1 V/cm for 15 hour in Tris/acetate/EDTA buffer. After electrophoresis, DNA was blotted by capillary action onto nitrocellulose (0.45 μm. Schleicher & Schuell). Filters were hybridized in formamide/dextran sulfate buffer by using standard method [Maniatis, T., et al., Molecular Cloning: A Laboratory Manual (Cold Spring Harbor Lab (1982)]. A 720-base-pair fragment of the HIV-1 LTR spanning the unique Xho I site and the HindIII site present in the R region of the HXBc2 molecular clone of HIV-1 was used as a probe for hybridization. The probe was labeled with [$^{32}$P]dCTP (>6000 Ci/mmol: 1 Ci=37 GBq: NEN/DuPont) by the random hexamer labeling procedure using a commercially available kit (United States Biochemicals).

Total unintegrated viral DNA was prepared from SupT1 cells 24 hours postinfection or from cells of human Jurkat T cell lines 6 days postinfection by a modified Hirt extraction. Agarose gel electrophoresis and Southern blotting and hybridization analyses of viral DNA were performed as described above.

PCR Analysis and DNA Sequencing.

Figure 7:
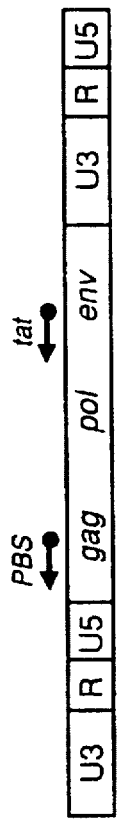
FIG. 7 is a schematic showing a method of screening for circle formation using PCR.
Figure 7:
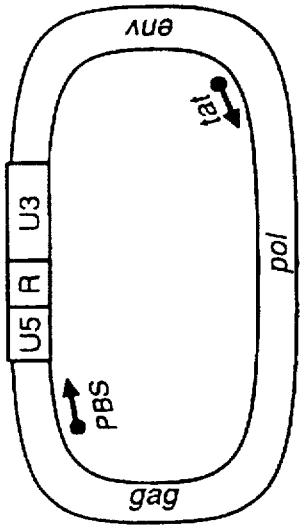
Figure 7:
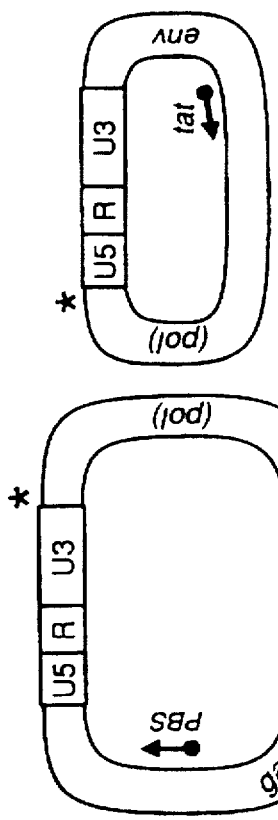
Figure 7:
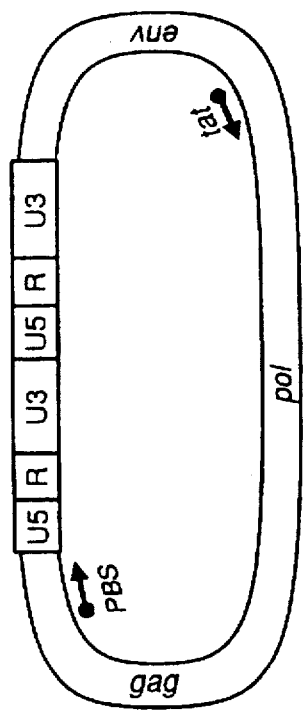
Figure 7:
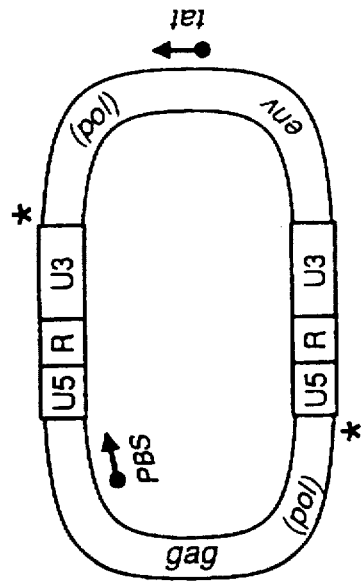

The following oligonucleotides were used for PCR: PBS, 5'-GTCGCCGCCCCTCGCCTC-3'(SEQ ID No. 1); tat, 5'-TCTGATGAGCTCTTCGTCGC-3'(SEQ ID No. 2); nef, 5'-GGGGGATCCGAAGAAGAAGGTGGAGAGCGA-3' (SEQ ID No. 3); R1, 5'-TGGCTAACTAGGGAACCCACTGCTTAAGCC-3' (SEQ ID No. 4); R2, 5'-AGAGCTCCCAGGCTCAGATCTGGTCTAACC-3' (SEQ ID No. 4). The locations of these primers in the viral genome are indicated in FIG. 7 by use of "*". One hundred microliter reactions contained 10 mM Tris hydrochloride (pH 8.3), 50 mM KCl, 1.5 mM MgCl$_2$, 0.001% (w/v) gelatin, 200 μM each dATP, dCTP, dGTP, and dTTP, 1 μM each of the indicated primer, and 2.5 units of AmpliTaq recombinant Taq DNA polymerase (Perkin Elmer Cetus Co., Norwalk, Conn.). For amplification of viral DNA from cytoplasmic extracts, each reaction contained approximately 1/30 the amount of DNA from a 3 ml extract. For amplification of viral DNA from Hirt extractions, each reaction contained DNA from the equivalent of 2×10$^6$ cells. An initial denaturation step at 98° C. was performed for 10 minutes. Thirty cycles of the PCR reaction were then performed with an annealing temperature of 60° C. for 1 minute, an extension temperature of 72° C. for 5 minutes, and a denaturation temperature of 95° C. for 1 minute. Reaction products were visualized following electrophoresis on 1% agarose gel containing ethidium bromide. For DNA sequence analysis of autointegration events, the smear of DNA products generated by PCR was cut out of the gel, the DNA purified from gel slices using Geneclean (Bio 101, Inc., La Jolla, Calif.) and sequenced directly by Sanger methods using the following primer, located in the U3 region of the virus: 5'-GCCCTGGTGTGTAGTTCTGC-3'(SEQ ID No. 6).

In Vitro Integration Reaction

Pst I-linearized (replicative form III) φX174 DNA, relaxed circular (replicative form II) φX174 DNA, and single-stranded M13 DNA were used as targets for the in vitro integration of viral DNA. Target DNA was added to cytoplasmic extracts of intected SupT1 cells to a concentration of 10 μg/ml, and reaction mixtures were incubated at 370° C. Reactions, were stopped by the addition of SDS and proteinase K.

RESULTS

Time Course of Viral DNA Synthesis

Figure 10A:
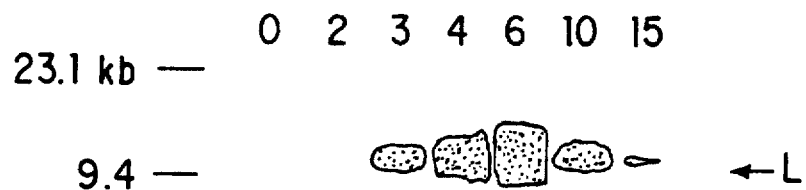
FIG. 10A shows the cytoplasm of infected cells and FIG. 10B shows the nuclear extract.
Figure 10B:
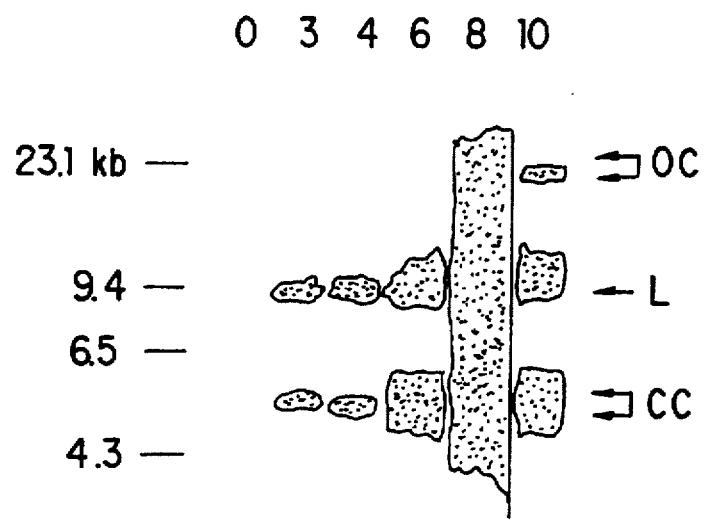

A synchronous infection system was used to study the synthesis of HIV-1 viral DNA in vivo. To achieve a synchronous infection, concentrated virus was placed onto rapidly dividing SupT1 cells, a human T-cell line that is highly susceptible to HIV-1 infection by virtue of a high surface density of the virus receptor CD4 molecule. Viral DNA formation was followed by Southern blot analysis of cytoplasmic extracts prepared from cells at various times after infection. Linear viral DNA was first detected approximately 2 hours after infection and reached peak levels between 4 and 6 hours (FIG. 10A). The numbers at the top of the lanes indicate hours after infection; arrows point to viral DNA species; OC, L, CC, open circular, linear, and closed circular DNAs, respectively. Between 8 and 15 hours after infection, the levels of linear DNA in the cytoplasm decreased, concurrent with the appearance of increasing levels of viral DNA in the nucleus. Viral DNA forms appeared in the nucleus as early as 4 hours after infection, with approximately equal amounts of linear and covalently closed circular (one LTR) forms present (FIG. 10B). By 10 hours after infection, all forms of viral DNA (linear, covalently closed circles with one LTR or two LTRs, and open circles with one LTR or two LTRs) were present in the nucleus (FIG. 10B). At no time were circular forms of viral DNA detectable in the cytoplasm, indicating that circularization of viral DNA occurred exclusively in the nucleus.

In Vitro Integration of Viral DNA

The ability of the linear viral DNA present in the cytoplasm of cells newly infected with HIV-1 to integrate into heterologous DNA targets in vivo was determined.

Figure 11:
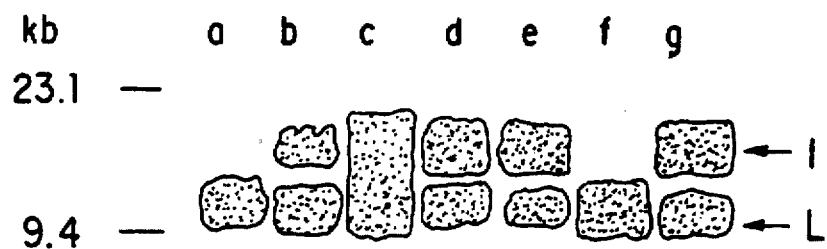
FIG. 11 shows in vitro integration of linear HIV-1-DNA.

Cytoplasmic extracts prepared from SupT1 cells 4 hours after infection with HIV-1 were incubated with exogenously added target DNA under integration reaction conditions. Products of the reactions were analyzed by Southern blot hybridization. The time course of integration into linear φX174 DNA target was determined. Target DNA was added to the extract and the reaction was stopped after 0,5,15,30, or 45 minutes of incubation at 37° C. (FIG. 11, lanes a–e, respectively). Purified linear viral DNA was incubated for 1 hour at 37° C. with cytoplasmic extract prepared from uninfected SupT1 cells (lane f). Integration into open circular φX174 DNA target; reaction product was linearized by digestion with the restriction endonucleas Aat II, which cleaves once in φX174 DNA sequences and does not recognize sequences in HIV-1 (lane g). Arrows in the Figure indicate the positions of viral DNA products. L, linear viral DNA:I, integration product. Integration was detected by the shift of linear viral DNA on Southern blots from the characteristic 9.7-kilobase (kb) position to a position corresponding to viral DNA plus target DNA. FIG. 11 (lane e) shows the product of integration of viral DNA into the linear form (replicative form III) of bacteriophage φX174 DNA. The position of the upper band in this lane corresponds to a molecule of a size consistent with the integration of linear HIV-1 DNA into a 5.4 kb target. FIG. 11 (lane g) shows the linear product of integration into relaxed circular (replicative form II) φX174 DNA after digestion with the restriction enzyme Aat II, which cuts once in φX174 DNA sequences and does not cut HIV-1 DNA. Densitometric scanning of the blots indicates that greater than 98% of the viral DNA molecules have integrated into the linear or relaxed circular targets after a 1-hour incubation. The time-course results demonstrate that the amount of integration products increased progressively during the incubation at 37° C. (FIG. 11, lanes a–e). The reaction was complete after 45 minutes of incubation. Hybridization of reaction products with a φX174-specific probe indicated that target DNA sequences were present in the 15-kb integration product (data not shown). The possibility that the integration product resulted from the end-to-end ligation of viral DNA and target DNA is not consistent with the results of integration into a relaxed circular DNA target, which contains no free ends. Furthermore, pretreatment of linear target DNA with alkaline phosphatase had no effect on the in vitro integration reaction (data not shown). Incubation of purified linear viral DNA with a linear DNA target in cytoplasmic extracts prepared from uninfected SupT1 cells failed to result in the formation of integration product (FIG. 11, lane f).

Table 1 outlines conditions that influenced the efficiency of the in vitro integration reaction. Integration in vitro occurred optimally at a monovalent location concentration of 150 mM. Concentrations of KCl of 250 mM or greater completely abolished detectable integration. An absolute requirement for magnesium for integration in vitro was demonstrated by the absence of detectable integration in buffer devoid of added $MgCl_2$ and containing 1 mM EDTA (see FIG. 13B, lane f). Integration occurred with equal efficiency at pH values ranging from 7.0 to 8.0, suggesting a broad pH optimum for the reaction. The integration activity was heat labile, as pretreatment of cytoplasmic extracts to 60° C. for 5 minutes prior to incubation at 37° C. completely abolished integration. Pretreatment of extracts with proteinase K prior to incubation with target DNA also abolished integration in vitro, further evidence that protein components of the extract are necessary for the integration of viral DNA. The single-stranded M13mp18 plasmid DNA did not serve as a target for in vitro integration, suggesting a requirement for a double-stranded target in the integration reaction (data not shown).

TABLE 1

Conditions affecting in vitro integration reaction

| Reaction condition(s)* | Relative activity, % of standard |
|---|---|
| Standard | 100 |
| $-Mg^2/+EDTA$ | 0 |
| NcCl (111111150 mM) | 100 |
| KCl (100 mM) | 85 |
| KCl (250 mM) | 0 |
| pH 7.0 | 100 |
| pH 8.0 | 100 |
| 60° C./5-min. preincubation | 0 |
| Proteinase K pretreatment/37° C./30 min | 0 |
| RNase A pretreatment/37° C./30 min | 100 |
| Open circular DNA treatment | 100 |
| Single-stranded DNA target | 0 |
| Uninfected cell extract +purified linear viral DNA +linear DNA target | 0 |

*Target DNA was present at 10 µg/ml in all samples
Extent of integration was determined by densitometric analysis of autoradiograms of Southern blots of integration reaction products.

Characterization of the in Vitro Integration Complex

Figure 12A:
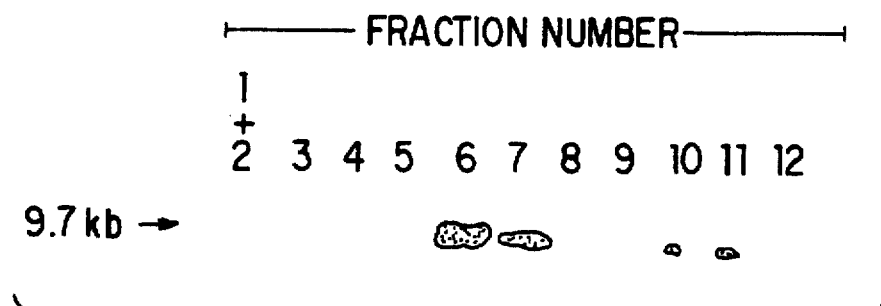
FIG. 12A shows cytoplasmic extracts.
Figure 12B:
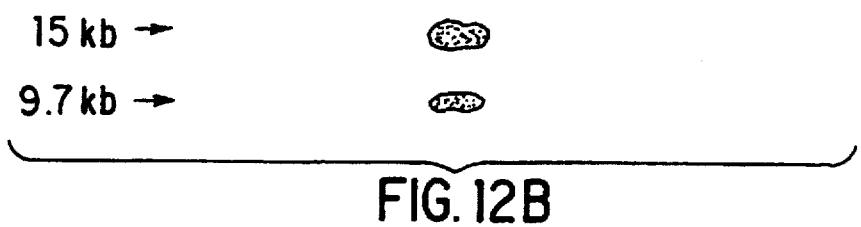
FIG. 12B shows in vitro integration of viral DNA in gradiant fractions.
Figure 12C:
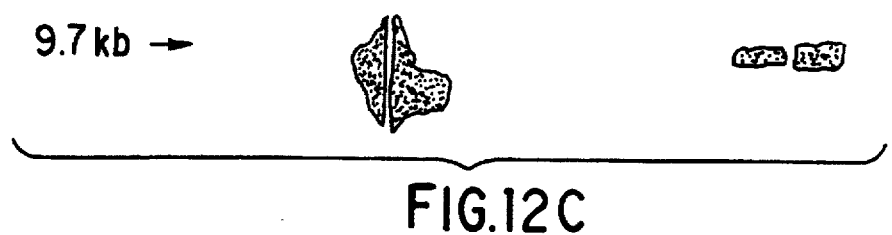
FIG. 12C shows sedimentation of deproteinated viral DNA.

Cytoplasmic extracts from HIV-1 infected SupT1 cells were analyzed by sucrose gradient sedimentation and gel-filtration chromatography to determine the physical properties of the in vitro integration activity. Cytoplasmic extracts (1 ml) shown in FIG. 12A prepared from SupT1 cells 4 hours after infection were layered onto 12-ml gradients of 15%–30% sucrose in buffer K and centrifuged at 35,000 rpm for 3 hours at 4° C. in a Beckman SW 41 rotor. Fractions (1 ml) were collected from the bottom of the gradient, deproteinated, and assayed for viral DNA by electrophoresis and Southern blot hybridization. Southern blotting was used to detect viral DNA in fractions collected from a 15%–30% (wt/vol) sucrose gradient. Viral DNA concentrations peaked near the middle of the gradient. Fractions containing viral DNA also contained the bulk of cellular rRNA, as detected by absorbance at 260 nM and agarose gel electrophoresis, indicating that the integration complex has a sedimentation profile similar to that of a ribosome. Arrows indicate the positions of linear viral DNA (9.7 kb) and integration products (15 kb). Viral DNA present in the gradient fractions was fully competent for integration in vitro into linear DNA targets (FIG. 12B). Conditions were the same as described above except that linearized φX174 DNA was added to gradient fractions to 10 µg/ml and incubated at 37° C. for 45 minutes prior to deproteination. Linear viral DNA, prepared from infected cells and deproteinated by treatment with proteinase K and phenol extraction prior to sedimentation, did not enter the sucrose gradient. Purified viral DNA mixed with cytoplasmic extracts prepared from uninfected SupT1 cells also failed to enter the sucrose gradient (FIG. 12C). Purified linear HIV-1 DNA was mixed with 1 ml of cytoplasmic extract from uninfected SupT1 cells and subjected to sedimentation as above. Numbers above the lanes in FIG. 12 indicate fraction numbers. Fraction 1 is the bottom of the gradient; fraction 12 is the top. Prior treatment of extracts with RNase A had no effect on the migration of viral DNA on sucrose gradients (data not shown).

Figure 13A:
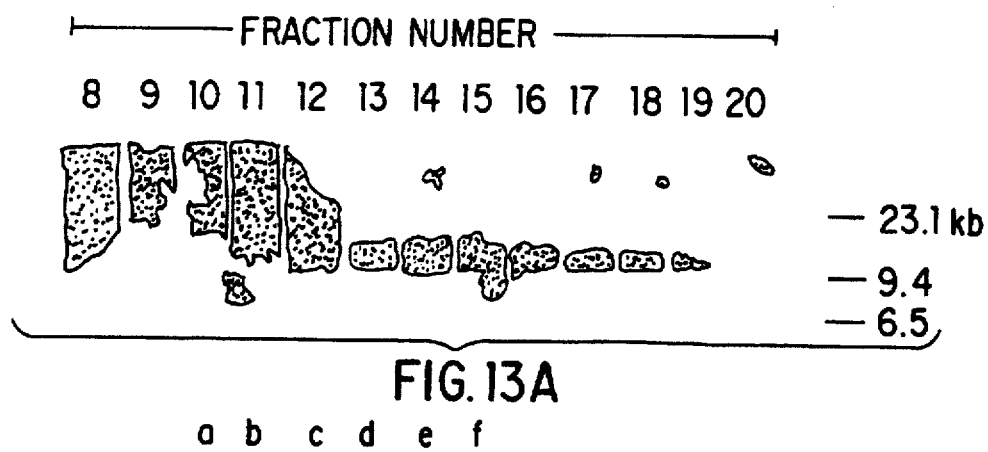
FIG. 13A shows the cytoplasmic extracts on a 7-ml Sephacryl S-1000 column.
Figure 13B:
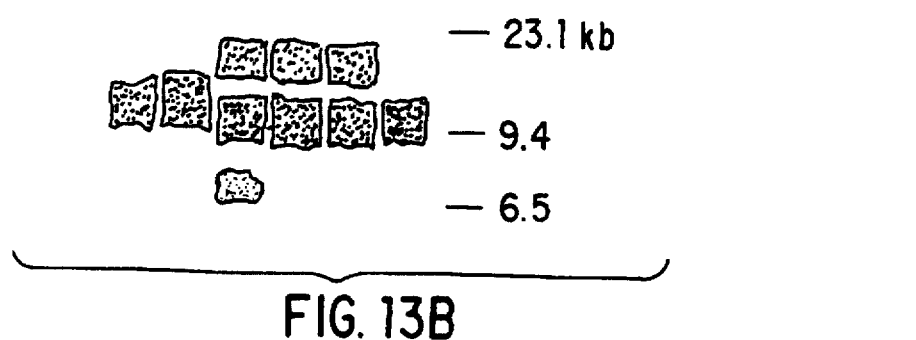
FIG. 13B shows in vitro integration of viral DNA in column fractions.
Figure 13:
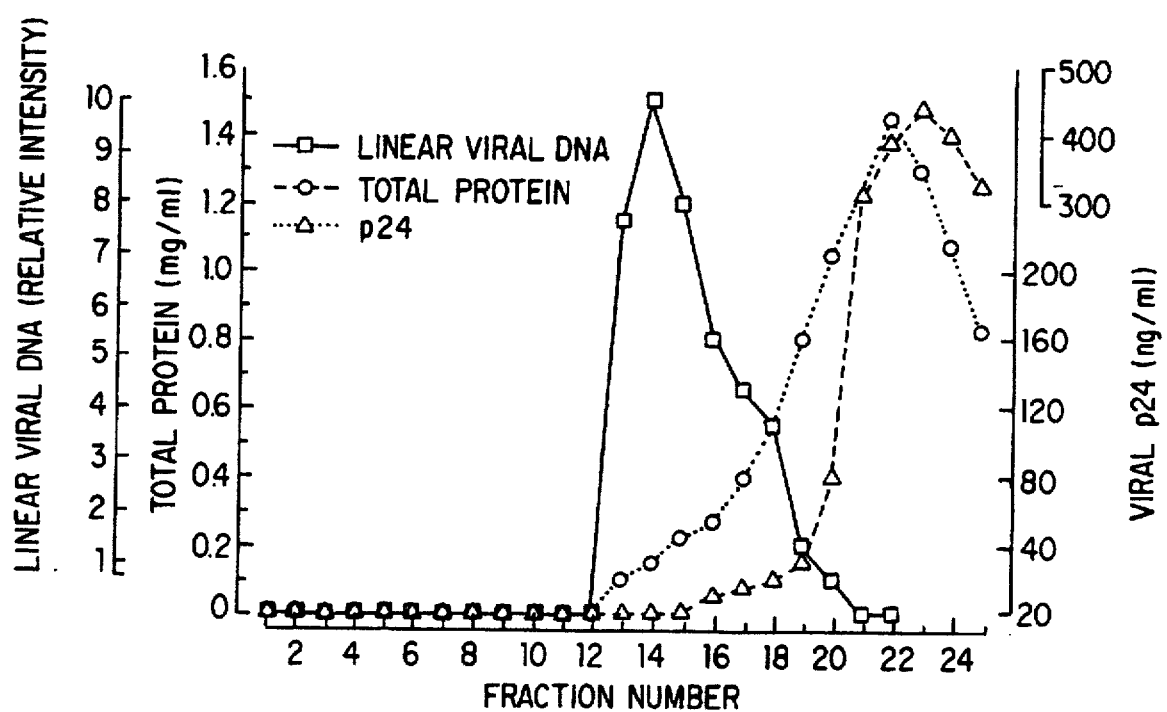
FIG. 13 shows Sephacryl S-1000 chromatography of viral DNA in cytoplasmic extracts.

Viral DNA present in the cytoplasmic extracts was separated from the bulk of cellular and viral proteins by Sephacryl S-1000 column chromatography. Southern blot analysis of the fractions collected from the column shows that the viral DNA eluted near the void volume, well separated from the peak of cellular protein eluted from the column (FIG. 13A and C). In FIG. 13A, cytoplasmic extracts (1 ml) were chromatographed on a 7 ml Sephacryl S-1000 (Pharmacia) column equilibrated in buffer K. Fractions (0.3 ml) were collected, deproteinated, and assayed for viral DNA by gel electrophoresis and Southern blot hybridization. Numbers above the lanes indicate fractions from the column. While FIG. 13C is a profile of linear viral DNA ( ), viral p24 (Δ), and total protein (o) eluted from the Sephacryl S-1000 column. Amount of viral DNA present per fraction is expressed as relative densitometric intensity of bands corresponding to integration products on autoradiogram shown in part A. Viral p24 concentration was determined by the HIV-1 strain HTLV-III p24 radioimmunoassay (DuPont). Total protein concentration in each fraction was determined by the BCA protein reagent microassay [Redinbaugh, M. G., et al, Anal. Biochem., 153: 267–271 (1986)]. Determination of protein concentration in each fraction indicated that the fractions with peak levels of viral DNA contained less than 1% of the total protein eluted from the column. The major viral core protein p24, detected by radioimmunoassay of column fractions, eluted from the column along with the bulk of cellular protein (FIG. 13C), and fractions that contained peak levels of viral DNA had no viral p24 detectable by this assay. Chromatography of the viral integration complex had no effect on the ability of the viral DNA to integrate in vitro. FIG. 13B shows that greater than 98% of the viral DNA molecules present in the peak fractions from the column were capable of integratng into a linear DNA target in vitro. In FIG. 13, lanes: a, viral DNA from extract prior to chromatography; b, same as lane a, except incubated at 37° C. for 45 minutes: c, d, and e, column fractions 13, 14, and 15, respectively, after incubation with linear φX174 (10 µpg/ml) at 37° C. for 45 minutes; f, in vitro integration reaction of viral DNA in fraction 13 of chromatograpohy as in A, except that $MgCl_2$ was omitted from the chromatography buffer, and 1 mM EDTA was added to the reaction mixture.

Screening for Compounds Which Affect Integration

Using the above described procedure, varying concentrations of a topoisomerase inhibiter, camptothecin, were added to the cytoplasmic extract. The cytoplasmic extract was then incubated for 90 minutes as described above, incubation was then stopped and integration measured.

In the absence of camptothecin, approximately 95% of the viral DNA was integrated into the target DNA. At a campthothocin concentration of 5 µM an inhibition of integration of about 50% was found. At a concentration of 50 µM an inhibition of integration of about 100% was found. Circularization of viral DNA in vitro.

Figure 14:
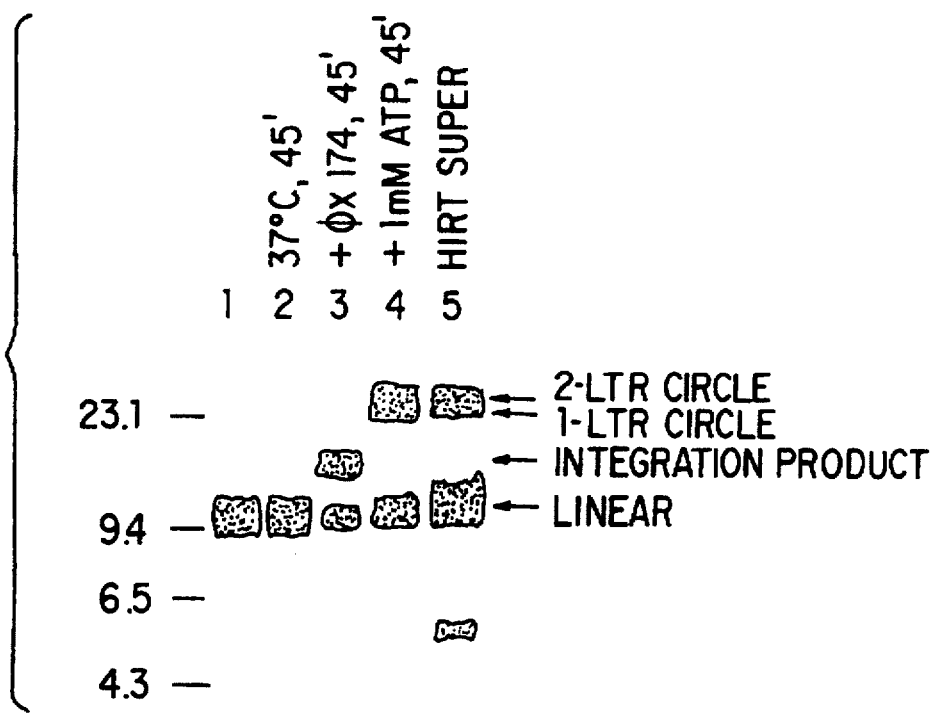
FIG. 14 shows viral DNA prepared from untreated extracts.
Figure 15:
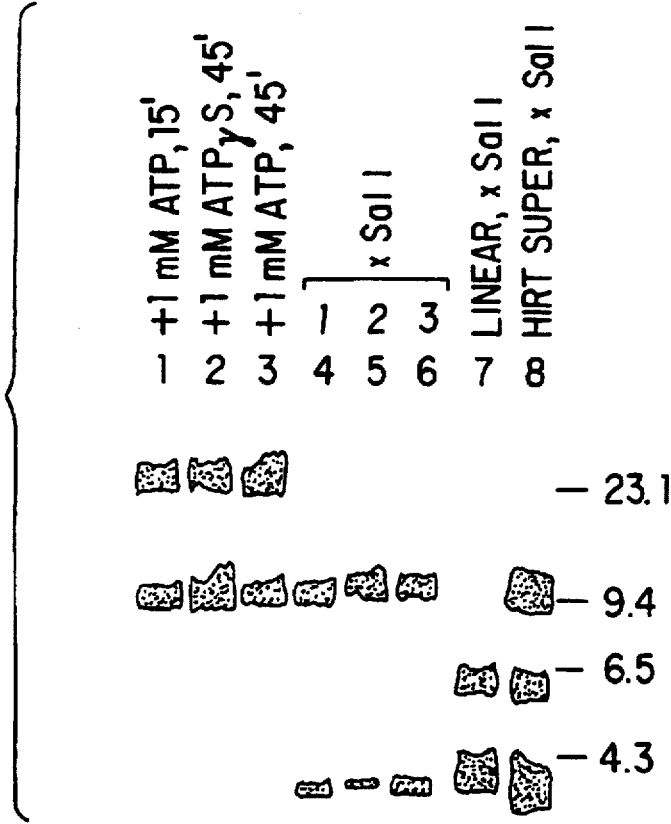
FIG. 15 shows restriction endonuclease analysis of circularization reaction products.
Figures 16, 17:
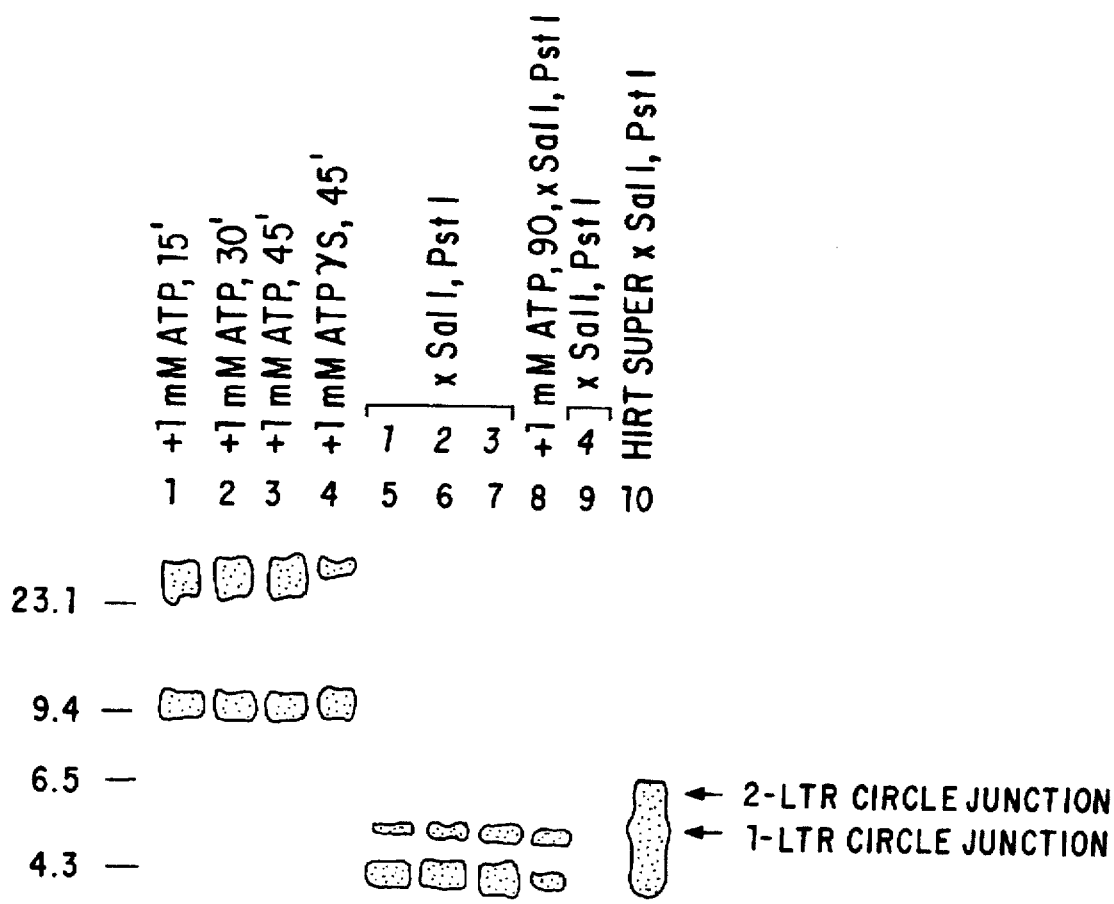
FIG. 16 shows a time course and restriction endonuclease analysis of circularization reaction products.
FIG. 17 shows cytoplasmic extracts with varying ATP levels.

Cell extracts were prepared from cells four to five hours after infection with HIV-1, using the above-described methods to yield fully functional viral preintegration complexes. Southern hybridization and restriction endonuclease analysis of the viral DNA prepared from the cytoplasmic extract 4 hours after infection with HIV-1 is shown in FIG. 14. In all cases, a HIV-1 LTR-containing DNA fragment was used as a hybridization probe. Therefore, only LTR-containing DNA fragments are detected. FIG. 14 shows viral DNA prepared from untreated extracts (lane 1), extracts incubated at 37° C. for 45 minutes (lane 2), extracts incubated with 650 ng/ml linear φX174 DNA at 37° C. for 45 minutes (lane 3), and extracts incubated with 1 mM ATP at 37° C. for 45 minutes (lane 4). Lane 5: Unintegrated viral DNA prepared by Hirt extraction of SupT1 cells infected 24 hours earlier with concentrated HIV-1. FIG. 15 shows the restriction endonuclease analysis of circularization reaction products. Viral DNA was purified from extracts incubated with 1 mM ATP for 15 minutes (lanes 1 and 4), with 1 mM ATP for 45 minutes (lanes 3 and 6), or with 1 mM ATPγS for 45 minutes (lanes 2 and 5). Lanes 1–3: uncut viral DNA; lanes 4–6: viral DNA was cut with SalI prior to electrophorosis. Lane 7: linear viral DNA, prepared from untreated extracts was digested with SalI prior to electrophorosis. Lane 8: unintegrated viral DNA prepared by Hirt extraction of infected cells, as described with respect to FIG. 14, digested with SalI prior to electrophoresis. FIG. 16 shows the time course and restriction endonuclease analysis of circularization reaction products. Lanes 1–3. Viral DNA prepared from extracts treated with 1 mM ATP for 15 minutes, 30 minutes and 45 minutes, respectively. Lane 4: Viral DNA prepared from extract treated with 1 mM ATPγS for 45 minutes. Lanes 5–7: products of reactions shown in lanes 1–3, respectively, digested with SalI and PstI prior to electrophoresis. Lane 8: SalI, PstI digestion of viral DNA prepared from extract treated with 1 mM ATP for 90 minutes. Lane 9: SalI, PstI digestion of reaction products shown in lane 4. Lane 10: SalI, PstI digestion of unintegrated viral DNA prepared by Hirt extraction of infected cells. Viral DNA present in the cytoplasmic extracts migrated as a single species when analyzed by agarose gel electrophoresis and Southern hybridization (FIG. 14, lanes 1 and 2). The extracts contained no detectable circular viral DNA, which is consistent with the above results and other reports that only full-length linear viral DNA is formed in the cytoplasm of cells newly infected with HIV-1 and other retroviruses.

Viral DNA present in the cytoplasmic extracts integrated into target DNA in vitro with very high efficiency (FIG. 14, lane 3).

ATP (1 mM) was added to the cytoplasmic extract in the absence of added target DNA. The addition of 1 mM ATP to cytoplasmic extracts resulted in the formation of two viral DNA species that migrated more slowly than the linear form of viral DNA on agarose gels (FIG. 14, lane 4). Formation of the slowly migrating DNA forms was dependent upon the addition of ATP; viral DNA in extracts incubated at 37° C. in the absence of added ATP remained linear (FIG. 14, lane 2). The electrophoretic mobilities of the two new DNA forms were identical to those observed for the 1-and 2-LTR open circular viral DNA molecules found in Hirt supernatants prepared from acutely infected cells (FIG. 14, lane 5). Digestion of the reaction products with SalI, which recognizes a single site in viral DNA, generated two novel DNA forms having electrophoretic mobilities expected of linear DNA molecules containing one or two LTRs, confirming the circular nature of the slowly migrating DNA forms (FIG. 15, lanes 1–6).

Conditions affecting the circularization of viral DNA in vitro.

Figure 19:
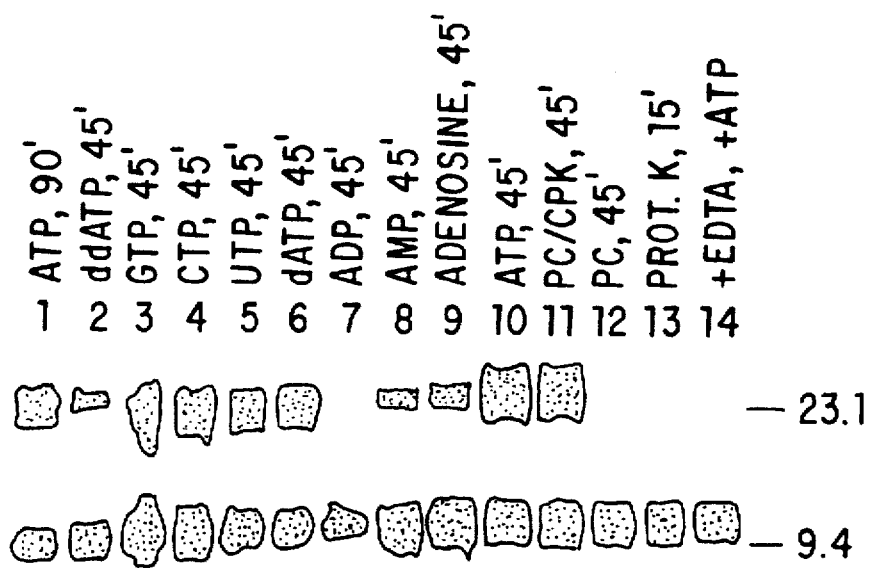
FIG. 19 shows the effect of circularization with different phosphates.

The formation of both forms of circular viral DNA was dependent on the presence of magnesium. Addition of 5 mM EDTA to extracts at the time of ATP addition abolished detectable circle formation (FIG. 19, lane 14). In addition, formation of both circular forms was dependent upon some cellular function present in the extracts, as pretreatment of extracts with proteinase K for 30 minutes prior to the addition of ATP abolished circle formation (FIG. 19, lane 13).

The amount of ATP added to the cellular extract was varied from 1 mM to 5 mM. Analysis of additional reaction parameters indicated that two circular viral DNA forms were generated by distinct mechanisms.

Figure 18:
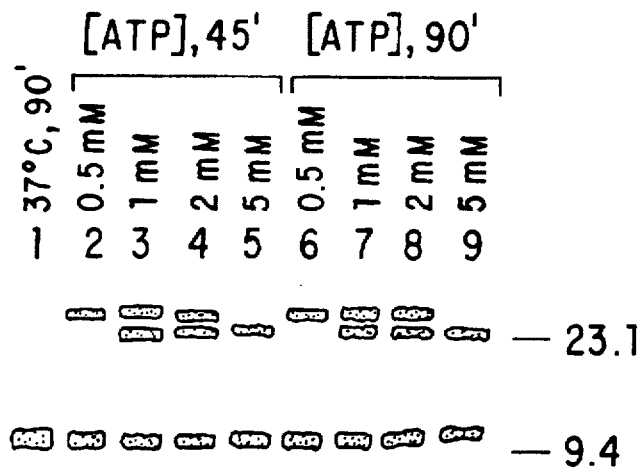
FIG. 18 shows cytoplasmic extracts with varying KCl levels.

FIGS. 17 and 18 shows the effect of ATP and KCl concentrations on the in vitro circularization reactions. FIG. 18 shows cytoplasmic extracts prepared 4 hours post-infection, ATP was added to a final concentration of 0.5 mM (lanes 2 and 6), 1 mM (lanes 3 and 7), 2 mM (lanes 4 and 8), or 5 mM (lane 5 and 9), and incubated at 37° C. for 45 minutes (lane 2–5) or 90 minutes (lanes 6–9). Lane 1: Viral DNA prepared from extract incubated in the absence of added ATP at 37° C. for 90 minutes.

FIG. 17 shows cytoplasmic extracts adjusted to a final KCl concentration of 100 mM (lane 1), 125 mM (lane 2), 150 mM (lane 3), 175 mM (Lane 4), 200 mM (lane 5), or 250 mM (lane 6), and ATP was added to a final concentration of 1 mM before incubating at 37° C. for 90 minutes. The formation of each circular species had a distinct ATP concentration optimum. Formation of 2-LTR circles was optimal in extracts containing 1 mM ATP, and was completely inhibited by a concentration of 5 mM ATP (FIG. 18, lanes 5 and 9). In contrast, 1-LTR circle formation peaked at 2mM ATP, and was considerable even at 5 mM ATP (lanes 4, 5, 8 and 9).

The salt concentration (KCl) added was also varied. Lower salt concentrations favored the formation of 1-LTR circles (FIG. 17). At a concentration of 100 mM KCl, 1-LTR circles were formed almost exclusively after incubation with ATP (lane 1). The most efficient formation of 1-LTR circles occurred in extracts containing 125 mM KCl (lane 2). In contrast, 2-LTR circle formation was most efficient at KCl concentration between 150 mM and 175 mM (lanes 4 and 4). At the higher salt concentrations, circular reaction products were most entirely of the 2-LTR form (lane 6).

A variety of nucleotides and related compounds were tested to see if they could induce the circularization of viral DNA in vitro. The above procedure was repeated but instead of ATP, 1 mM of other nucleotide or related compound was used. See FIG. 19, which shows the results of such tests to induce the circularization of viral DNA in vitro. Lanes 1–9: Cytoplasmic extracts were incubated with added ATP (lane 1), ddATP (lane 2), GTP (lane 3), CTP (lane 4), UTP (lane 5), dATP (lane 6), ADP (lane 7), AMP (lane 8), or adenosine (lane 9). In all cases, compounds were added to a final concentration of 1 mM, and incubated at 37° C. for 45 minutes, except for the reaction shown in lane 1, which was incubated for 90 minutes. Lanes 10–12, extracts were incubated for 45 minutes at 37° C. after the addition of 1 mM ATP (lane 10), 10 mM phosphocreatine and 200 μg/ml creatine phosphokinase (lane 11), or 10 mM phosphocreatine (lane 12). Lane 13: Proteinase K was added to the cytoplasmic extract and incubated at 37° C. for 10 minutes, then ATP was added to 1 mM final concentration and incubation continued for 45 minutes. Lane 14: EDTA was added to a final concentration of 5 mM at the time of addition of ATP to 1 mM, and incubated at 37° C. for 45 minutes. Deoxyadenosine triphosphate induced both circular forms with an efficiency comparable to ATP (FIG. 19, lane 6). All of the other NTPs and dNTPs induced the formation of 2-LTR circles, but induced the formation of only a small amount of the 1-LTR circular form (lanes 3–5, and data not shown). Similarly, the nonhydrolyzable analogue of ATP, ATPγS, as well as the 2', 3'-dideoxynucleoside, the 2', 3'-dideoxynucleoside, triphosphates, ddATP, ddCTP, dd-GTP and ddTTP, induced the formation of 2-LTR circles, but were unable to induce detectable amounts of the 1-LTR circular forms (lane 2, and data not shown). No circular DNA forms were observed as products of reactions containing the nucleoside diphosphates ADP or GDP, the nucleoside monophosphate AMP, the nucleosides adenosine, guanosine, cytosine, azidothymidine, or cordycepin, or the free bases adenine, guanine, or uracil (FIG. 19, lanes 7–9, and data not shown). Both 1-LTR and 2-LTR circles were formed following the addition of phosphocreatine and creating phosphokinase to the cytoplasmic extracts, presumably due to the synthesis of ATP from endogenous ADP (lane 11).

Restriction Enzyme Analysis of Circular Viral DNA.

The structures of the circular DNA molecules formed in vitro were analyzed by restriction enzyme digestion and compared to the structures of circular molecules formed in vivo. Digestion of the in vitro circularization reaction products with SalI and PstI, which each cut viral DNA once, generated two novel LTR-containing junction fragments not present in digests of linear viral DNA (FIG. 16, lanes 5–7). These fragments had the same size as the LTR-containing junction fragments produced by digestion of viral DNA prepared from Hirt supernatants of acutely infected cells (lane 10). The autoradiographic intensity of the 1-LTR junction fragment produced by digestion of the in vitro circularization reaction products were identical to the intensity of the uncut 1-LTR circular molecule (lane 7). In contrast, the intensity of the fragment encoding the 2-LTR junction was reproducibly several fold lower than that of the uncut 2-LTR circle (lane 7). Time course analysis demonstrated that the amount of 1-LTR junction fragment formed in the in vitro reaction increased in proportion to the amount of 1-LTR circular DNA formed (FIG. 16, lanes 1–7). On the other hand, the amount of 2-LTR junction fragment increased at a rate far slower than the rate of increase of the amount of 2-LTR circular DNA (lanes 1–7). These results indicate that all of the 1-LTR circular molecules formed in vitro resulted from the formation of a novel 1-LTR junction, while only a small fraction of the 2-LTR circles formed in vitro could be explained by simple end-to-end joining of the linear viral DNA. In addition, digestion of the circularization reaction products with these enzymes generated high background smears not visible in the digests of linear viral DNA, consistent with the presence of a heterogeneous population of circular molecules generated by autointegration.

As mentioned previously, circular viral DNA formed by the addition of ATPγS to cell extracts was exclusively of the 2-LTR type, with no detectable 1-LTR circles produced. Digestion of ATPγS-induced circles with SalI and PstI demonstrated the absence of 1-LTR junction fragments (FIG. 16, lane 9). In addition, no new 2-LTR junction fragments were detected, demonstrating the absence of simple 2-LTR circles among the reaction products. Instead, a high background of heterogeneous LTR-containing fragments was produced, indicating that the 2-LTR circles formed in the presence of the nonhydrolyzable ATP analogue were entirely the products of autointegration.

PCR Analysis of Circular Viral DNA.

Figure 8:
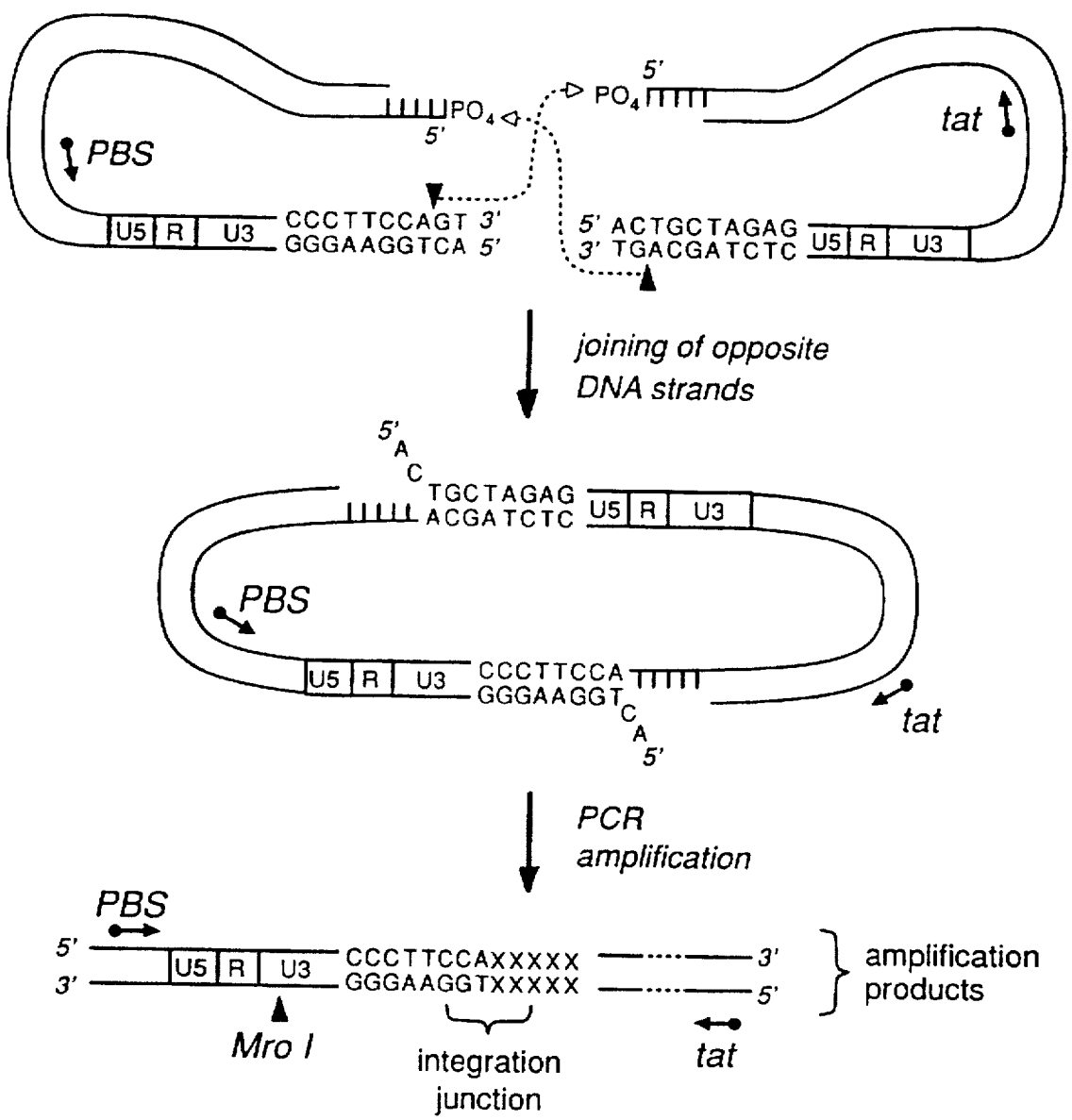
FIG. 8 is a schematic showing how to amplify autointegration events by PCR to screen for autointegration circles.

PCR analysis of the circularization reaction products also confirms of the formation of 2-LTR circles by autointegration. The strategy used for detection of autointegration events is diagrammed in FIGS. 7 and 8. Both amplification primers used anneal to the sense strand of viral DNA, one in the viral primer binding site (PBS) region upstream of the gag gene, the other in the tat gene. Since they anneal to the same strand of DNA, these primers will not amplify any sequences on linear or 1-LTR circular viral DNA, or 2-LTR circles formed by end-to-end ligation. However, these primers will anneal to opposite DNA strands on those circular autointegration products that result from the joining of opposite strands of viral DNA at the site of integration. Therefore, 2-LTR circles formed by autointegration will direct the amplification of a population of molecules of heterogeneous lengths when the PBS and tat primers are used. All of the amplified sequences are predicted to have a full LTR sequence at the end defined by the PBS amplification primer.

PCR amplification of viral DNA purified from extracts that had been incubated with 1 mM ATP using the PBS and tat primers generated a mixture of DNA fragments of heterogeneous lengths (FIG. 24, A lane 1). In contrast, no detectable products were made when viral DNA from extracts incubated at 37° C. for 1 hour in the absence of added ATP was the substrate for PCR (lane 2). Digestion of the amplification products with MroI, which cuts at a single site in the U3 region of the viral LTR, generated a 425 bp fragment, demonstrating that the heterogeneous population of amplified molecules contained a viral LTR at one end (lane 3).

Figure 25:
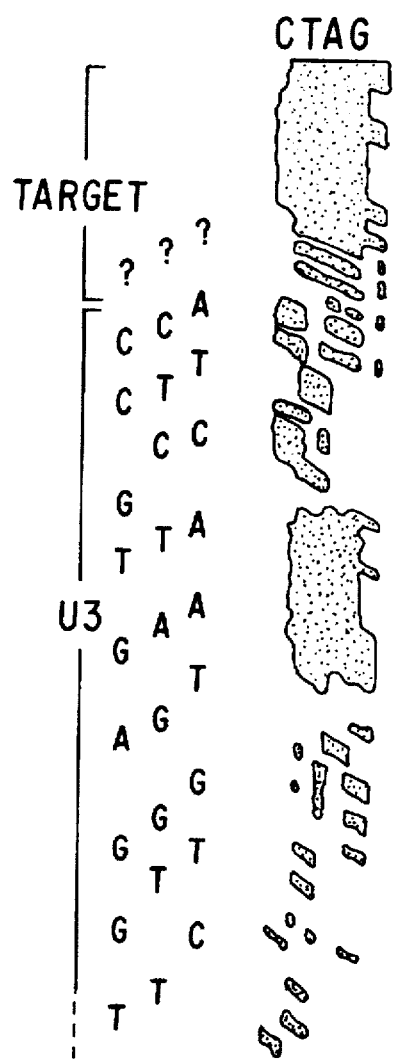
FIG. 25 shows DNA sequence analysis of a PCR amplification product.

DNA sequence analysis provided further evidence that the PCR amplification products resulted from authentic integration events. The heterogeneous products of amplification were purified from agarose gel slices after electrophoresis and sequenced using a primer that hybridized to the LTR near the U3 terminus. The sequence of the amplified molecules was homogeneous up to the CA dinucleotide present at the end of the U3 region of the LTR; thereafter, the sequence became random (FIG. 25). This CA dinucleotide is the site of joining of viral DNA to target DNA during integration in vivo and in vitro. The randomization of sequence beyond this point results from integration at many target sites within the viral DNA. The identification of the highly conserved CA dinucleotide as the site of LTR joining to target sequence is strong evidence that the recombination events that lead to the formation of 2-LTR circles in vitro are mediated by the viral integrase.

PCR analysis was also performed on circular viral DNA formed in vivo using the primers designed to detect autointegration events. Unintegrated viral DNA was prepared by Hirt extraction of SupT1 cells 24 hours after infection with HIV-1, at a time when circular viral DNA can be detected in the nucleus, and subjected to PCR analysis using the primers described above. Again, a smear of DNA fragments was generated by amplification, and a discrete 425 bp band was produced from the amplification products by digestion with MroI, indicating that autointegration events occur naturally during the course of viral replication (FIG. 15, B, lanes 1–4).

Figure 26:
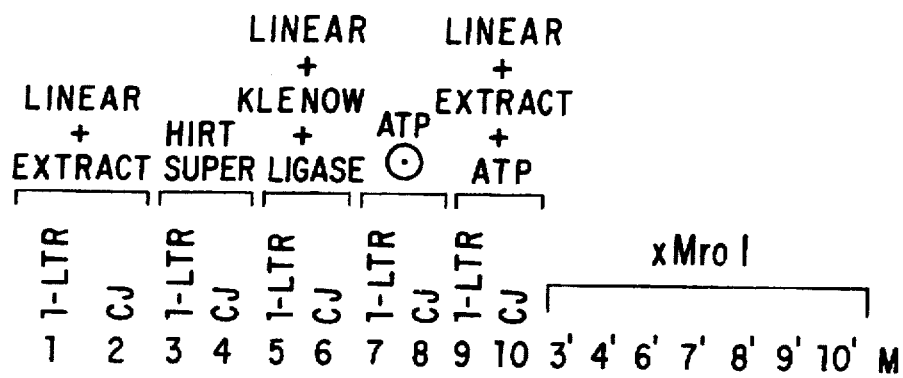
FIG. 26 shows an upper portion and a schematic produced from the amplification products digested with MroI.

The formation of authentic 1-LTR circles in vitro was also demonstrated by PCR amplification of reaction products. These experiments were performed using primers in the viral primer binding site (PBS) region upstream of the gag gene and in the viral nef gene, each of which directed DNA synthesis toward the respective terminus of the linear DNA molecule (FIG. 3). These primers did not amplify any sequences when viral DNA from the untreated extracts was used as a substrate in the PCR reaction (FIG. 26, lane 1).

However, a DNA fragment having the size expected for a 1-LTR circle junction was generated when viral DNA prepared from extracts treated with 1 mM ATP was used for amplification (lane 7). The amplified product was cut once by the restriction endonuclease MroI, which recognizes a single site in the U3 region of the LTR, generating fragments with sizes expected of the viral LTR (lane 7'). The same product was produced when these primers were used to amplify circular viral DNA prepared from Hirt supernatants of acutely infected cells (lane 3) demonstrating that the 1-LTR circles formed in vitro are similar in structure to the 1-LTR circles formed in vivo.

Figure 27:
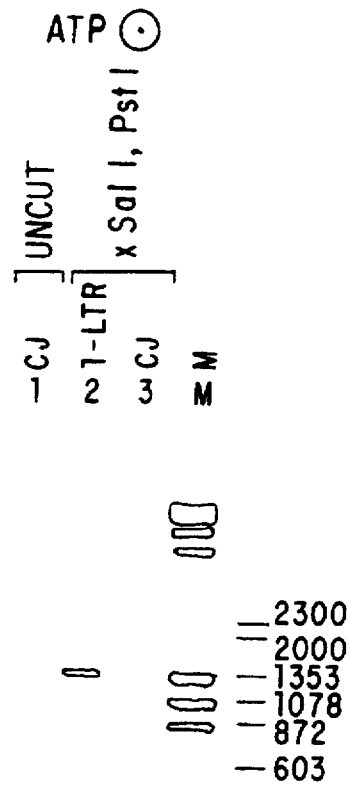
FIG. 27 shows PCR of 1-and 2-LTR circles using the $R_1$ and $R_2$ primers.

Additional rounds of PCR amplification were necessary to detect the presence of a DNA fragment corresponding to the 2-LTR junction fragment when viral DNA from Hirt supernatants of infected cells were used, presumably due to the lower concentration of 2-LTR circles as compared to 1-LTR circles in these preparations (data not shown). Similarly, 2-LTR junction fragments were not readily detected among the amplification products of circular viral DNA formed in vitro, most likely due to the low concentration of simple 2-LTR circles and competition by the other forms of circular viral DNA (1-LTR circles and 2-LTR circles formed by autointergration) present at much higher concentrations. Therefore, the formation of 2-LTR junctions was analyzed using primers capable of specifically amplifying 2-LTR junction sequences. For these experiments, two primers which anneal to opposite DNA strands in the R region of the viral LTR were used (diagrammed in FIGS. 5 and 7). These primers are expected to amplify only viral genome-length DNA molecules from linear and 1-LTR circular viral DNA. In addition to the genome length fragment, simple 2-LTR circles are also predicted to direct the amplification of a small DNA fragment having the length of the viral LTR. Digestion of circular DNA with SalI prior to amplification will prevent the formation of the long DNA molecules, but will have no effect on the amplification of the DNA fragment specific to simple 2-LTR circles. See FIG. 27, lane 1 is uncut, lanes 2–3 were digested with SalI and PstI. Amplification of SalI digested DNA prepared from Hirt supernatants of acutely infected cells using these primers resulted in the synthesis of the expected LTR-sized DNA fragments (FIG. 26, lane 4). A DNA fragment of the same size was detected when SalI digested circular viral DNA formed in vitro in the presence of added ATP was used as a substrate for PCR (data not shown). However, detection of this fragment was obscured by a very high background of amplification products of heterogeneous lengths (FIG. 26, lane 8). A population of DNA molecules of heterogeneous lengths is predicted to be produced form 2-LTR circles formed by autointegration when the R region primers are used, in the same manner described earlier for the detection of autointegration events. Amplification of the specific 2-LTR junction fragment from the products of the in vitro circularization reaction was most likely competed by the higher concentration of 2-LTR circles formed by autointegration relative to simple 2-LTR circles. Note that a weaker background smear of amplification products, in addition to the strong fragment corresponding to the 2-LTR junction, was also produced when circular viral DNA from the nucleus of infected cells was amplified using these primers (lane 4). This observation is consistent with a low but detectable level of autointegration in vivo.

Circularization Mediated by Partially Purified Preintegration Complexes.

Figure 20:
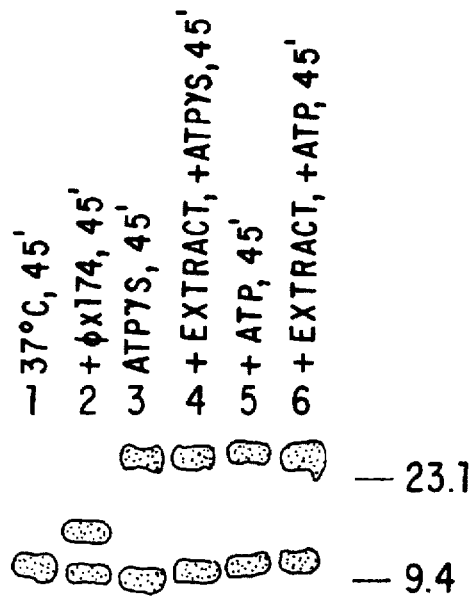
FIG. 20 shows the effect on circularization by using partially purified preintegration complexes.
Figure 21:
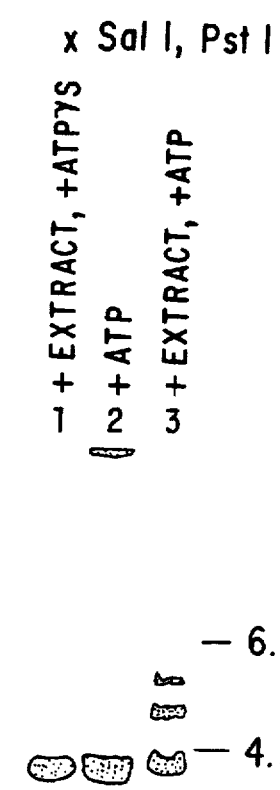
FIG. 21 shows restriction endonuclease analysis of partially purified cytoplasmic extracts.

The linear viral DNA present in cytoplasmic extracts is a part of the nucleoprotein preintegration complex that can be separated from the bulk of cellular proteins by gel filtration chromatography [Farnet and Haseltine, *J. Virol.*, 65: 1910–1915 (1991)]. Preintegration complexes were partially purified by Sephacryl S400 column chromatography and tested for the ability to mediate the circularization of viral DNA. See FIG. 20. Cytoplasmic extracts (1 ml, vol) were fractionated by Sephacryl S-400 gel filtration chromatography as previously described. The void volume fractions of the column, containing the peak of viral DNA, were pooled (total volume, 1.5 ml) and incubated as follows with the results shown in FIG. 20. Lane 1: column fractions were incubated at 37° C. for 45 minutes; lane 2: linear φX174 DNA was added to column fractions to a final concentrations of 650 ng/ml and incubated at 37° C. for 45 minutes; lane 3: ATPγS was added to column fractions and incubated at 37° C. for 45 minutes; lane 4: same as lane 3, except that an equal volume of cytoplasmic extract from uninfected SupT1 cells was added prior to incubation; lane 5: ATP was added to column fractions to a final concentration of 1 mM and incubated at 37° C. for 45 minutes; lane 6: same as lane 5, except that an equal volume of cytoplasmic extract from uninfected SupT1 cells was added prior to incubation. FIG. 21 shows the restriction endoclease analysis of reaction products. Lane 1: products of the reaction shown in FIG. 20, lane 4, digested with SalI and PstI; lane 2: products of the reaction shown in FIG. 20, lane 5, digested with SalI and PstI; lane 3: products of the reaction shown in FIG. 20, lane 6, digested with SalI and PstI. Addition of 1 mM ATP to column fractions containing the peak of viral DNA resulted in the formation of only the 2-LTR circular DNA form (FIG. 20, lane 5). Restriction enzyme analysis indicated that the 2-LTR circular products resulted entirely from autointegration events, as no new 2-LTR junctions were detected (FIG. 21, lane 2). The addition of cytoplasmic extracts from uninfected SupT1 cells to column fractions containing viral DNA restored the ability to form 1-LTR circles (FIG. 20, lane 6), indicating that a cellular factor was responsible for 1-LTR circle formation. In addition, a small amount of new 2-LTR junction fragment was also detected in digests of circular products following the addition of uninfected cell extracts (FIG. 21, lane 3), indicating that a cellular DNA ligase was responsible for generating some of the 2-LTR circular products. Pretreatment of uninfected SupT1 extracts with proteinase K prior to addition of the column fractions abolished the ability of the extracts to restore 1-LTR and simple 2-LTR circle formation (data not shown). The formation of all types of circular produts was dependent upon the addition of ATP, as viral DNA in column fractions remained linear during incubation at 37° C. in the absence of added ATP (FIG. 20, lane 1), regardless of the addition of uninfected SupT1 cell extracts. Hydrolysis of ATP appeared to be necessary for the formation of 1-LTR and simple 2-LTR circles by column purified preintegrating complexes, as addition of ATPγS, to column fractions, both in the presence and absence of uninfected cell extracts, resulted in the exclusive formation of autointegration 2-LTR circles (FIG. 20, lanes 3 and 4). This result is consistent with the earlier observation that circular molecules induced by the addition of ATPγS to unfractionated extracts are entirely the result of autointegration events.

Circularization of Purified Linear Viral DNA.

Further evidence of a role for host proteins in the formation of the 1-LTR and simple 2-LTR circular forms of viral DNA was obtained by testing the ability of uninfected cell extracts to mediate the circularization of purfied viral DNA. Linear viral DNA was prepared from cytoplasmic extracts of uninfected cells by SDS-proteinase K treatment and phenol extraction. The purfied DNA was added to cytoplasmic extracts prepared form uninfected SupT1 cells, in the presence or absence of added ATP. New, slowly migrating DNA species were detected following incubation of viral DNA with uninfected cell extracts and added ATP (FIG. 22, lane 2).

The most abundant of the new DNA forms comigrated with the 1-LTR circular DNA molecules formed in infected cell extracts while a small amount of product migrating as 2-LTR circles could also be detected. (FIG. 22, lanes 2 and 3). Restriction enzyme analysis confirmed the formation of new 1-LTR and 2-LTR junction fragments in these reactions (data not shown). PCR analysis, using the strategies described earlier for the amplification of 1-LTR circle junctions and 2-LTR circle junctions confirmed the formation of authentic 1-LTR and simple 2-LTR circular DNA molecules in these reactions (FIG. 26, lanes 9 and 10). No amplification products were detected when linear viral DNA incubated in uninfected cell extracts in the absence of added ATP was used as a substrate for PCR (lanes 1, 2). Furthermore, no DNA fragments of heterogeneous lengths were produced upon amplification of reaction products using the primers designed to detect autointegration events (data not shown), nor was the background smear evident in amplification of the specific 2-LTR junction fragment (lane 10), indicating that none of the 2-LTR circles formed in the reactions were result of autointegration. The latter observation is expected, given the absence of the viral integrase in these reactions.

Figure 22:
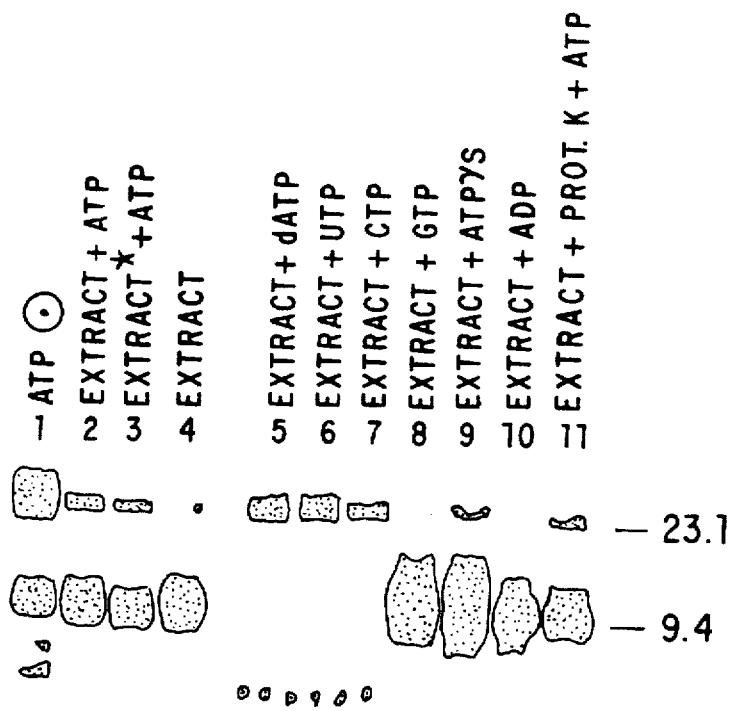
FIG. 22 shows purified viral DNA with varying phosphates.

ATPγS, which did not induce the formation of 1-LTR or simple 2-LTR circular DNA in cytoplasmic extracts of infected cells, also failed to induce the circularization of purified linear viral DNA when added along with extracts from uninfected cells (FIG. 22, lane 9). Deoxyadenosine triphosphate, UTP, and CTP were able to induce the formation of 1-LTR circles when added to uninfected cell extracts containing purified linear viral DNA, but failed to induce the formation of detectable 2-LTR circles (lanes 5–7). The absence of simple 2-LTR circles was confirmed by the inability to detect 2-LTR circle junctions by PCR analysis of the reaction products (not shown).

Figure 23:
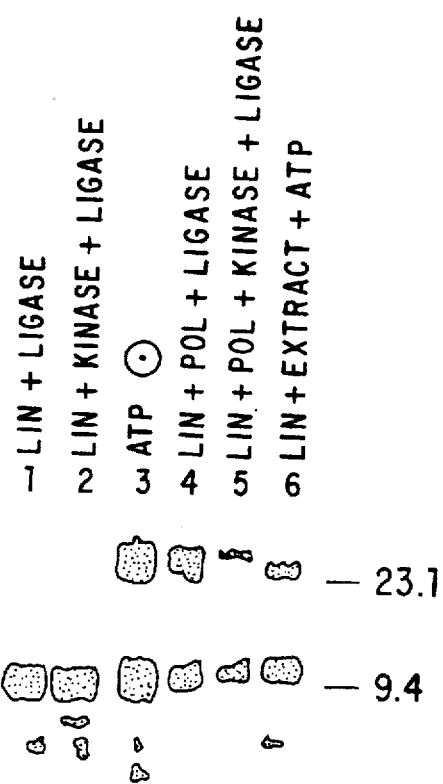
FIG. 23 shows the effect on circularization using deproteinated DNA and DNA ligase.

The results presented above indicated that formation of simple 2-LTR circles from linear viral DNA required ATP hydrolysis. None of the other nucleoside triphosphates tested, nor ATPγS, was able to substitute for ATP in the reaction. FIG. 22 shows circularization of purified linear viral DNA in vitro. Linear viral DNA was purified from cytoplasmic extracts of cells 4 hours post-infection as described above. In FIG. 22, a purified linear viral DNA was added to cytoplasmic extracts from uninfected SupT1 cells and incubated at 37° C. for 45 minutes. The uninfected SupT1 cells used for the preparation of extracts were either untreated (lanes 3–11) or cultured in the presence of 10 ng/ml phorbol 12-myristate 13-acetate for six hours prior to extraction (lane 2). Lane 1 shows the viral DNA formed in extracts of infected cells incubated with 1 mM ATP for 45 minutes, as size standards. Lanes 2–11: reaction products following incubation of purified linear viral DNA in uninfected extracts containing 1 mM ATP (lanes 2 and 3), nothing added (lane 4), 1 mM dATP (lane 5), 1 mM UTP (lane 6), 1 mM CTP (lane 7), 1 mM GTP (lane 8), 1 mM ATPγS (lane 9), or 1 mM ADP (lane 10). Lane 11: uninfected SupT1 cell extract was treated with proteinase K for 10 minutes at 37° C., then linear viral DNA was added and incubation continued for 45 minutes. In FIG. 23, lanes 1, 2, 4 and 5: purified linear viral DNA was incubated with T4 DNA ligase (lane 1), T4 polynucleotide kinase and T4 DNA ligase (lane 2), Klenow fragment of E. coli DNA polymerase I and T4 DNA ligase (lane 3), or Klenow fragment, T4 polynucleotide kinase, and T4 DNA ligase (lane 4). Lanes 3 and 6: in vitro circularization reaction products generated in cell extracts, included as size standards. Lane 3: cytoplasmic extracts from infected cells were incubated with 1M ATP for 45 minutes; lane 6: purified linear viral DNA was incubated with cytoplasmic extract from uninfected SupT1 cells in the presence of 1 mM ATP for 45 minutes. The possibility that a host DNA ligase was responsible for the formation of the simple 2-LTR circles was examined by testing the ability of phage T4 ligase to catalyze the circularization of linear viral DNA. The data in FIG. 23 shows that T4 DNA ligase alone was unable to ligate the ends of the linear DNA molecules (lanes 1 and 2). However, products migrating as 2-LTR circles were formed when the Klenow fragments of E. coli DNA polymerase was added to the reaction mixture in addition to the DNA ligase (lanes 3 and 4). Restriction endonuclease analysis of the reaction products formed in the presence of both Klenow fragment and T4 DNA ligase confirmed the formation of new 2-LTR junctions (not shown). These results indicate that the linear viral DNA molecules are not blunt-ended, but can be converted to blunt-ended molecules through the action of a DNA polymerase. This observation is consistent with previous reports that linear viral DNA prepared from cells infected with the murine leukemia virus [Fujiwara and Mizuuchi, Cell, 54:497–504 (1988) and HIV-1 [Pauza, Virology, 179:886–887 (1990)] consists of a mixture of molecules that are either blunt-ended or recessed by two nucleotides at each 3'-terminus. The removal of the two terminal nucleotides is mediated by the viral integrase as a necessary step in the process of integration [Roth et al., Cell 58: 47–54 (1989)]. Given the high efficiency of integration of the viral DNA molecules present in the extracts described here, it is likely that nearly all of the linear molecules possess 3'-recessed termini at the time of purification. This would explain the requirement of DNA polymerase for the subsequent joining of the ends of viral DNA by DNA ligase.

Circularization Versus Intergration.

Figure 28:
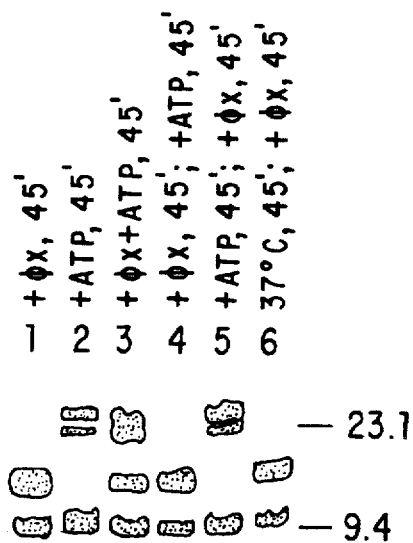
FIG. 28 shows circularization versus integration with target DNA.
Figure 29:
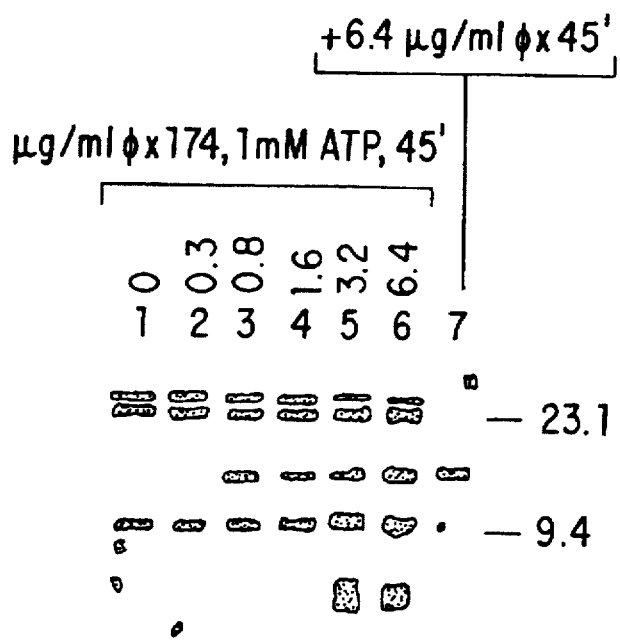
FIG. 29 shows the competition between circularization and integration with varying levels of target DNA.
Figure 30:
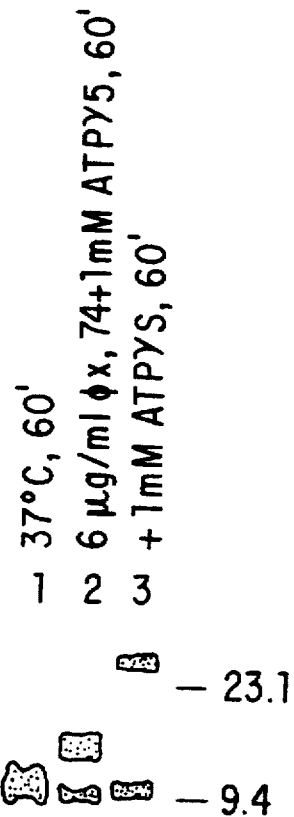
FIG. 30 shows the competition between integration and circularization using ATPγS.

Circularization of the linear viral DNA present in cytoplasmic extracts was competitive with integration into heterologous DNA targets (FIG. 28). In FIG. 28, cytoplasmic extracts from infected cells were incubated at 37° C. as follows: Lane 1; incubation with 10 μg/ml φX174 DNA for 45 minutes, lane 2, incubation with 1 mM ATP for 45 minutes; lane 3, incubation with 10 μ/ml φX174 DNA and 1 mM ATP for 45 minutes; lane 4, incubation with 10 μg/ml φX174 DNA for 45 minutes, followed by incubation with 1 mM ATP for 45 minutes; lane 5, incubation with 1 mM ATP for 45 minutes, followed by incubation with 10 μg/ml φX174 DNA for 45 minutes; lane 6, incubation with nothing added for 45 minutes, followed by incubation with 10 μg/ml φX174 DNA for 45 minutes. In FIG. 29, lanes 1–6, cytoplasmic extracts from infected cells were incubated at 37° C. for 45 minutes in the presence of 1 mM ATP and φX174 DNA at a concentration of 0 μg/ml (lane 1), 0.3 μg/ml (lane 2), 0.8 μg/ml (lane 3), 1.6 μg/ml (lane 4), 3.2 μg/ml (lane 5), or 6.4 μg/ml (lane 6). Lane 7, extract incubated with 6.4 μg/ml φX174 DNA for 45 minutes in the absence of added ATP. In FIG. 30, cytoplasmic extracts from infected cells were incubated at 37° C. for 60 minutes with nothing added (lane 1), with 6.4 μg/ml φX174 DNA and 1 mM ATPγS (lane 2), or with 1 mM ATPγ alone (lane 3). Addition of both ATP and target DNA to extracts resulted in the formation of both circular and integrated viral DNA (FIG. 28, lane 3). Under these conditions, the amount of circular or integrated product produced was reduced as compared to incubation with ATP alone or target DNA alone (FIG. 28, lanes 1 and 2). Furthermore, circularization of viral DNA was prevented by preincubation of extracts with target DNA for 45 minutes prior to the addition of ATP (lane 4). Likewise, integration of viral DNA into target DNA was prevented by preincubation of extracts with ATP prior to the addition of target DNA (lane 5).

The absence of circular viral DNA following addition of ATP to extracts preincubated for 45 minutes with target DNA was expected, given that nearly all of the linear molecules have integrated into target by this time (FIG. 28, lane 1). However, the viral DNA that remained linear following a 45 minute incubation with ATP was unable to integrate during a subsequent incubation with target DNA (lane 5). Preincubation of the extract at 37° C. in the absence of ATP did not diminish the ability of the viral DNA to integrate into target DNA during a subsequent incubation (lane 6). These results indicate that the preincubation with ATP in some way inhibited the ability of the linear DNA molecules to integrate into target DNA.

Addition of increasing concentrations of target DNA to extracts containing 1 mM ATP indicated that integration of viral DNA into target competed most effectively with the formation of 2-LTR circles (FIG. 29, lanes 1–6). Greatly reduced amounts of 2-LTR circles were formed when target DNA was present at 6.4 μMg/ml in extracts containing 1 mM ATP as compared to incubation in the presence of ATP and the absence of target DNA (FIG. 29, compare lanes 1 and 6). Under these conditions, the small amount of 2-LTR circles formed were almost entirely simple 2-LTR circles, as the autoradiographic intensity of the 2-LTR circle junction fragment produced by restriction enzyme digestion of reaction products was nearly identical to that of the uncut 2-LTR circles (data not shown). These results indicate that integration into target DNA competed very effectively with the autointegration reaction, such that autointegration 2-LTR circles were not formed in the presence of high concentrations of target DNA. As a further test of this hypothesis, target DNA and ATPγS were added simultaneously to extracts from infected cells. Target DNA at concentration of 6 ng/ml was able to completely inhibit the formation of 2-LTR circles by ATPγS, which were previously shown to result exclusively from autointegration (FIG. 30, lane 2).

Analysis of the formation of 1-LTR circles in the presence of increasing amounts of target DNA indicated that the presence of target DNA did not inhibit 1-LTR circle formation (FIG. 29, lanes 2–6). Indeed, in some cases enhanced 1-LTR circle formation was observed when target DNA was added to cell extracts in addition to ATP. Addition of very high concentrations (≧30 ng/ml) of target DNA to extracts containing 1 mM ATP greatly reduced the amounts of both 2-LTR and 1-LTR circular DNA formed (FIG. 28, lane 3).

It is evident that those skilled in the art, given the benefit of the foregoing disclosure, may make numerous modifications thereof, and departures from the specific embodiments described herein, without departing from the inventive concepts, and the present invention is to be limited soley by the scope and spirit of the appended claims.

We claim the following:

1. A method of determining the level of cellular integration of a DNA sequence which comprises:

(a) transfecting a cell in vitro with a DNA sequence which is capable of integrating into a target DNA sequence (transfected DNA sequence);

(b) incubating the transfected DNA sequence in the cell;

(c) separating the cellular cytoplasmic fluid from nuclear extract of the cell before the transfected DNA sequence chronically infects the cell;

(d) adding the target DNA sequence to the fluid; and (e) determining the level integration of the transfected DNA sequence.

2. The method of claim 1 wherein the DNA sequence which is capable of integrating into a target DNA sequence is an oncogenic sequence or a viral sequence.

3. The method of claim 2 wherein the DNA sequence which is capable of integrating into a target DNA sequence is a viral sequence.

4. A method of claim 3 wherein the viral sequence is a pathogenic DNA sequence.

5. The method of claim 4 wherein the pathogenic DNA sequence is a pathogenic retroviral-derived DNA sequence.

6. The method of claim 5 wherein the target DNA sequence is a mammallian DNA sequence.

7. The method of claim 5 wherein the retroviral-derived DNA sequence is derived from a lentivirus.

8. The method of claim 7 wherein the lentivirus is HIV-1, HIV-2, or SIV.

9. The method of claim 1, wherein the target DNA sequence is a mammallian DNA sequence.

10. The method of claim 9, wherein the target DNA sequence is a human DNA sequence.

11. The method of claim 1, wherein the cytoplasmic fluid is from a cell that is susceptible to HIV infection and the DNA sequence which is capable of integrating into a target DNA sequence is HIV-1 or HIV-2.

12. The method of claim 11, wherein the DNA sequence which is capable of integrating into a target DNA sequence is added by infecting the whole cell which is susceptible to HIV infection with HIV virus, incubating the cells for a sufficient time and under sufficient conditions to permit viral replication and thereafter separating the cytoplasmic fluid from the cell.

13. The method of claim 12 wherein the cytoplasmic fluid is separated from the cell at the first peak of viral replication.

14. A method for determining if a factor affects circularization activity which comprises:

(a) contacting cellular cytoplasmic fluid in vitro with a DNA sequence which is capable of circularization, wherein the fluid does not contain a target DNA sequence;

(b) adding a predetermined factor to the fluid; and (c) determining whether circularization has occurred.

15. The method of claim 14, wherein the circularization is caused by autointegration.

16. The method of claim 14, wherein the DNA sequence which is capable of circularization is an oncogenic sequence or a viral sequence.

17. The method of claim 16, wherein the DNA sequence which is capable of circularization is a pathogenic viral sequence.

18. The method of claim 17, wherein the viral sequence is a retroviral-derived sequence.

19. The method of claim 18, wherein the retroviral sequence is derived from a lentivirus.

20. The method of claim 19, wherein the lentivirus is HIV-1, HIV-2, or SIV.

21. A method for screening for factors which will enhance a circularization activity rather than integration which comprises contacting cellular cytoplasmic fluid with a DNA sequence which is capable of circularization activity under conditions which permit circularization, adding a target DNA sequence to the fluid, adding a predetermined factor to the fluid, and thereafter determining the amount of (1) integration, (2) integration and circularization or (3) circularization that has occurred.

22. The method of claim 21 wherein the DNA sequence which is capable of circularization is an oncogenetic sequence or a viral sequence.

23. The method of claim 21 wherein the DNA which is capable of circularization is a pathogenic viral sequence.

24. The method of claim 23, wherein the pathogenic viral sequence is a pathogenic retroviral-derived sequence.

25. The method of claim 24 wherein the pathogenic retroviral-derived sequence is derived from a lentivirus.

26. The method of claim 25 wherein the lentivirus is HIV-1, HIV-2, or SIV.

27. The method of claim 21 wherein the circularization is caused by autointegration.

* * * * *

UNITED STATES PATENT AND TRADEMARK OFFICE
CERTIFICATE OF CORRECTION

PATENT NO. : 5,759,768
DATED : June 2, 1998
INVENTOR(S) : William A. Haseltine, Christopher M. Farnet It is certified that error appears in the above-identified patent and that said Letters Patent is hereby corrected as shown below:

Col. 1, before line 4, insert -- -The above invention was made, in part, with support from NIH Grant No. AI24845 and AI31388 and the United States Government has certain rights thereto.- -

Signed and Sealed this

Third Day of August, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GTCGCCGCCC CTCGCCTC                                                              1 8

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TCTGATGAGC TCTTCGTCGC                                                      2 0

( 2 ) INFORMATION FOR SEQ ID NO:3:

( i ) SEQUENCE CHARACTERISTICS:
        ( A ) LENGTH: 30 base pairs (B) TYPE: nucleic acid
(C) STRANDEDNESS: single
(D) TOPOLOGY: linear (xi) SEQUENCE DESCRIPTION: SEQ ID NO:3:

GGGGGATCCG AAGAAGAAGG TGGAGAGCGA                    30

(2) INFORMATION FOR SEQ ID NO:4:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (xi) SEQUENCE DESCRIPTION: SEQ ID NO:4:

TGGCTAACTA GGGAACCCAC TGCTTAAGCC                    30

(2) INFORMATION FOR SEQ ID NO:5:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (xi) SEQUENCE DESCRIPTION: SEQ ID NO:5:

AGAGCTCCCA GGCTCAGATC TGGTCTAACC                    30

(2) INFORMATION FOR SEQ ID NO:6:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (xi) SEQUENCE DESCRIPTION: SEQ ID NO:6:

GCCCTGGTGT GTAGTTCTGC                               20